US006899880B2

(12) United States Patent
Stephens et al.

(10) Patent No.: US 6,899,880 B2
(45) Date of Patent: May 31, 2005

(54) PORIN B (PORB) AS A THERAPEUTIC TARGET FOR PREVENTION AND TREATMENT OF INFECTION BY CHLAMYDIA

(75) Inventors: Richard Stephens, Orinda, CA (US); Aya Kubo, Sunnyvale, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/155,947

(22) Filed: May 24, 2002

(65) Prior Publication Data

US 2003/0021801 A1 Jan. 30, 2003

Related U.S. Application Data

(63) Continuation of application No. 09/775,195, filed on Jan. 31, 2001, now abandoned.

(60) Provisional application No. 60/179,592, filed on Feb. 1, 2000.

(51) Int. Cl.$^7$ ...................... A61K 39/02; G01N 33/554; G01N 33/569; C12P 21/06

(52) U.S. Cl. ................... 424/190.1; 435/7.32; 435/69.1

(58) Field of Search ...................... 424/190.1; 435/7.32, 435/69.1

(56) References Cited

U.S. PATENT DOCUMENTS

| | | | |
|---|---|---|---|
| 4,267,170 | A | 5/1981 | Seawell |
| 4,271,146 | A | 6/1981 | Seawell |
| 5,242,686 | A | 9/1993 | Chu et al. |
| 5,656,271 | A | 8/1997 | MacDonald et al. |
| 5,716,793 | A | 2/1998 | MacDonald et al. |
| 5,725,863 | A | 3/1998 | Daniels et al. |
| 5,770,714 | A | 6/1998 | Agabian et al. |
| 5,821,055 | A | 10/1998 | Agabian et al. |
| 5,840,297 | A | 11/1998 | MacDonald et al. |
| 5,972,350 | A | 10/1999 | Atherton et al. |
| 6,166,177 | A | 12/2000 | Probst et al. |

FOREIGN PATENT DOCUMENTS

| | | | | |
|---|---|---|---|---|
| WO | WO 94/06827 A1 | 3/1994 | | |
| WO | WO 96/31236 A1 | 10/1996 | | |
| WO | WO 97/41889 A1 | 11/1997 | | |
| WO | WO 98/02546 A2 | 1/1998 | | |
| WO | WO 98/10789 A1 | 3/1998 | | |
| WO | WO 98/58953 A2 | 12/1998 | | |
| WO | WO 99/10005 A1 | 3/1999 | | |
| WO | WO 99/28475 A2 | 6/1999 | | |
| WO | WO 99/28475 | * 6/1999 | ........... | C12N/15/31 |

OTHER PUBLICATIONS

Marshal, E. " Gene Therapy's Growing Pains" Science, vol. 269, pp. 1050–1055, Aug. 25, 1995..*

Seq ID No 2 ( PorB ) search report.*

Allen, et al. "*A single peptide from the major outer membrane protein of chlamydia trachomatis elicits T cell help for the production of antibodies to protective determinants*", The Journal of Immunology vol. 147(2): 674–679 (1991).

Bavoil, et al. "*Role of disulfide bonding in outer membrane structure and permeability in chlamydia trachomatis*", Infection and Immunity vol. 44(2): 479– 485 (1984).

Berman, et al. "*Recommendations for the prevention and management of chlamydia trachomatis infections*", The Morbidity and Mortality Weekly Report vol. 42(RR–12): 1–102 (1993).

Caldwell, et al. "*Purification and partial characterization of the major outer membrane protein of chlamydia trachomatis*", Infection and Immunity vol. 31(3): 1161–1176 (1981).

Everett, et al. "*Architecture of the cell envelope of chlamydia psittaci 6BC*", Journal of Bacteriology vol. 177(4): 877–882 (1995).

Fan, et al. "*Antigen conformation dependence of chlamydia trachomatis infectivity neutralization*", The Journal of Infectious Diseases vol. 176: 713–721 (1997).

Filip, et al. "*Solubilization of the cytoplasmic membrane of escherichia coli by the ionic detergent sodium–lauryl sarcosinate*", Journal of Bacteriology vol. 115(3): 717–722 (1973).

Iliffe–Lee, et al. "*Regulation of carbon metabolism in chlamydia trachomatis*", Molecular Microbiology vol. 38(1): 20–20 (2000).

Ivens, et al. "*A physical map of the Leishmania major Friedlin genome*", Genome Research vol. 8(2): 135–145 (1998).

Kalman, et al. "*Comparative genomes of chlamydia pneumoniae and chlamydia trachomatis*", Nature Genetics vol. 21: 385–389 (1999).

Kubo, et al. "*Characterization and functional analysis of PorB, a chlamydia porin and neutralizing target*", Molecular Microbiology vol. 38(4): 772–780 (2000).

Moulder, et al. "*Interaction of chlamydiae and host cells in vitro*", Microbiological Reviews vol. 55(1): 143–190 (1991).

Newhall, et al. "*Biosynthesis and disulfide cross–linking of outer membrane components during the growth cycle of chlamydia trachomatis*", Infection and Immunity vol. 55(1): 162–168 (1987).

(Continued)

*Primary Examiner*—Rodney P Swartz
*Assistant Examiner*—Khatol S Shahnan-Shah
(74) *Attorney, Agent, or Firm*—Bozicevic, Field & Francis LLP; Carol L. Francis; Edward Baba

(57) ABSTRACT

The present invention features the use of PorB polypeptide as a therapeutic agent. In specific embodiment the invention features a chlamydial vaccine based on a PorB polypeptide, as well as methods for induction of a protective immune response against infection by *Chlamydia* and *Chlamydiophila*. The invention further features methods for identifying agents that affect PorB function such as in transport of α-ketoglutarate and which are effective as anti-chlamydial chemotherapeutic agents.

10 Claims, 8 Drawing Sheets

OTHER PUBLICATIONS

Read, et al. "*Genome sequences of chlamydia trachomatis MoPn and chlamydia pneumoniae AR39*", Nucleic Acids Research vol. 28(6): 1397–1406 (2000).

Sanchez–Campillo, et al. "*Identification of immunoreactive proteins of chlamydia trachomatis by western blot analysis of a two–dimensional electrophoresis map with patient sera*", Electrophoresis vol. 20:2269–2279 (1999).

Sardinia, et al. "*Developmental regulation of the cysteine–rich outer–membrane proteins of murine chlamydia trachomatis*", Journal of General Microbiology vol. 134: 997–1004 (1988).

Stephens, et al. "*High–resolution mapping of serovar–specific and common antigenic determinants of the major outer membrane protein of chlamydia trachomatis*", J. Exp. Med. vol. 167:817–831 (1988).

Stephens, et al. "*Genome sequence of an obligate intracellular pathogen of humans: Chlamydia trachomatis*", Science vol. 282: 754–759 (1998).

Stephens, et al. "*Antigen Variation of Chlamydia trachomatis*", In J.W. Moulder (ed.), Intracellular Parasitism, CRC Press, Boca Raton, pp. 51–62.

Su, et al. "*Protective efficacy of a parentally administered MOMP–derived synthetic oligopeptide vaccine in a murine model of chlamydia trachomatis genital tract infection: Sertum neutralizing IgG antibodies do not protect against chlamydial genital tract infection*", Vaccine vol. 13(11): 1023–1032 (1995).

Thylefors, et al. "*Global data on blindness*", Bulletin of World Health Organization vol. 73(1): 115–121 (1995).

Tuffrey, et al. "*Heterotrophic protection of mice against chlamydial salpingitis and colonization of the lower genital tract with a human serovar F isolate of chlamydia trachomatis by prior immunization with recombinant serovar L1 major outer–membrane protein*", Journal of Gen Microbiology vol. 138: 1707–1715 (1992).

Wyllie, et al. "*The major outer membrane protein of chlamydia psittaci functions as a porin–like ion channel*", Infection and Immunity vol. 66(11): 5202–5207 (1998).

GenBank Accession No. AAC68308 published Oct. 30, 2000.

GenBank Accession No. AE001342 AE001273, deposited Oct. 30, 2000.

GenBank Accession No. H71479 published Oct. 8, 1999.

GenBank Accession No. NP_225049 published Sep. 10, 2001.

GenBank Accession No. CAC44728 published Jul. 25, 2001.

GenBank Accession No. H81742 published May 11, 2000.

GenBank Accession No. AAF38966 published May 26, 2000.

GenBank Accession No. NP_220232 published Sep. 10, 2001.

GenBank Accession No. P38006 published Aug. 20, 2001.

GenBank Accession No. NP_296470 published Oct. 2, 2001.

GenBank Accession No. Q9PLL3 published Oct. 16, 2001.

* cited by examiner

FIG. 1

10 20 30 40
CTD PorB M S S K L V N Y L R L T F L S F L G I A S T S L D A M P A G N P A F P - - V I P
CTD MOMP M K K L L K S V L V F A A L S - - - - S A S S L Q A L P V G N P A E P S L M I D 50 60 70 80
CTD PorB G I N I E Q K N A C S F D L C N S Y D V L S A L S G N L K L C F C G D Y I F S E
CTD MOMP G I L W E G F G G D P C D P C A T W C D A I S M R V G Y Y G D F V F D R V L K T 90 100 110 120
CTD PorB E A Q V K D V P V V T S V T T A G - - V G P S P D I T S T T K T R N F D L V N C
CTD MOMP D V N K E F Q M G A K P T T D T G N S A A P S T L T A R E N P A Y G R H M Q D A 130 140 150 160
CTD PorB N L N T N C V A V A F S L P D R S L S A I P L F D V S F E V K - - V G G L K Q Y
CTD MOMP E M F T N A A C M A L N I W D R F D V F C T L G A T S G Y L K G N S A S F N L V 170 180 190 200
CTD PorB Y R L P M N A Y R D F T S E P L N S E S E V T D G M I E V Q S N Y G F V W D V S
CTD MOMP G L F G D N E N Q K T V K A E S V P N M S F D Q S V V E L Y T D T T F A W S V G 210 220 230 240
CTD PorB L K K V I W K D G V S F V G V G A D Y R H A S - - - - - - - - - C P I D Y I I A
CTD MOMP A R A A L W E C G C A T L G A S F Q Y A Q S K P K V E E L N V L C N A A E F T I 250 260 270 280
CTD PorB N S - - - - - - - - - - - - - Q A N P E V F I A D S D G K L N F K E W S V C V G
CTD MOMP N K P K G Y V G K E F P L D L T A G T D A A T G T K D A S I D Y H E W Q A S L A 290 300 310 320
CTD PorB L T T Y V N D Y V L P Y L - - - - - - - A F S I G S V S R Q A P D - - - - - - -
CTD MOMP L S Y R L N - M F T P Y I G V K W S R A S F D A D T I R I A Q P K S A T A I F D 330 340 350 360
CTD PorB - - - - - - - - - - - - - - - - - D S F K K L E D R F T N L K F K V R K I T S S H
CTD MOMP T T T L N P T I A G A G D V K T G A E G Q L G D T M Q I V S L Q L N K M K S R K

SEQ ID NO:2
370 380 390 400
CTD PorB R G N I C I G A T N Y V A D N F F Y N V E G R W G S Q R A V N V S G G F Q F
CTD MOMP S C G I A V G T T I V D A D K Y A V T V E T R L I D E R A A H V N A Q F R F
SEQ ID NO:3

Adipate
Glutarate
α-ketoglutarate
Glutamate
Aconitate
Citrate
Succinate
Malate
Oxaloacetate
Malonate

PORIN B (PORB) AS A THERAPEUTIC TARGET FOR PREVENTION AND TREATMENT OF INFECTION BY CHLAMYDIA

CROSS-REFERENCE TO RELATED APPLICATION

This application is a continuation of prior U.S. patent application Ser. No. 09/775,195, filed Jan. 31, 2001, now abandoned; which application claims the benefit of U.S. provisional application Ser. No. 60/179,592, filed Feb. 1, 2000, which applications are hereby incorporated by reference.

STATEMENT AS TO FEDERALLY SPONSORED RESEARCH

This invention was made, at least in part, with a government grant from the National Institutes of Health (Grant Nos. NIH grants AI40250, AI39258, and AI42156). Thus, the U.S. government may have certain rights in this invention.

FIELD OF THE INVENTION

The invention relates generally to the field of diagnosis, treatment, and prevention of infectious disease, particularly to prevention of infectious disease caused by the bacterial pathogen *Chlamydia* and *Chlamydophila* (formerly classified as, for example, *C. psittacci* and *C. pneumoniae*).

BACKGROUND OF THE INVENTION

Chlamydiae are obligate intracellular pathogens that cause a spectrum of diseases including trachoma, the leading cause of preventable blindness worldwide, as well as a variety of sexually transmitted diseases such as lymphogranuloma venereum, urethritis, cervicitis, endometritis, and salpingitis (Thylefors et al. (1995) Bull W H O 73:115–121). For example, *Chlamydia trachomatis* is considered the world's most common sexually transmitted bacterial pathogen (Schachter and Grayston (1998) Presented at the Ninth international symposium on human chlamydial infection, Napa, Calif.; World Health Organization, 1996, Global prevalence and incidence of selected curable sexually transmitted diseases: overview and estimates). Currently an estimated 400 million people have active infectious trachoma, while 90 million have a sexually transmitted disease caused by *C. trachomatis* (World Health Organization, 1996). *Chlamydia pneumoniae* usually infects the lungs and causes no more than a mild cold; however, it can travel to the blood vessels and thrive in clots, causing heart disease. Diseases caused by *Chlamydia* represent significant health problems worldwide.

Growth of *Chlamydia* generally depends on the acquisition of host ATP and other high-energy metabolites from the host (Moulder et al. (1991) Microbiol. Rev. 55:143–90). Chlamydiae have the enzymatic machinery for the Embden-Meyerhoff pathway (EMP), the pentose phosphate pathway (PPP), and the tricarboxylic acid (TCA) cycle (Kalman et al. (1999) Nat. Genet. 21:385–9; Stephens et al. (1998) Science 282:754–9). The TCA in chlamydia is incomplete in that the host lacks three enzymes: citrate synthase, aconitase, and isocitrate dehydrogenase (Kalman et al., ibid,; Stephens et al., ibid.). This observation suggests that the glutamate and α-ketoglutarate are obtained from the host cell since these can not be synthesized by the bacterium. It has been shown that chlamydiae utilize glucose as the major source of carbon, but that dicarboxylates also serve to support chlamydial viability and growth ((Iliffe-Lee et al. (2000) Mol. Microbiol. 38:20–30).

Treatment for *Chlamydia* infection typically involves administration of an antimicrobial drug such as azithromycin, doxycycline, ofloxacin, erythromycin, or amoxicillin (Centers for Disease Control and Prevention. Recommendations for the prevention and management of *Chlamydia trachomatis* infections. Morb Mortal Wkly Rep 1993; 42 (RR-12): 1–102). These conventional treatments are problematic for several reasons, including patient non-compliance with multi-day, multi-dose regimens and side effects such as gastrointestinal problems. Furthermore, treatment of *Chlamydia* with existing antimicrobial drugs may lead to development of drug resistant bacterial strains, particularly where the patient is concurrently infected with other common bacterial infections.

In addition, chlamydial infections often have no overt symptoms, so irreversible damage can be done before the patient is aware of the infection. Therefore, prevention of the infection is considered the best way to protect from the damage caused by *Chlamydia*. Therefore, the development and production of effective chlamydial vaccines, more effective treatments once infection is established, and sensitive and specific diagnostic assays are important public health priorities.

*Chlamydia* have a unique developmental growth cycle with morphologically distinct infectious and reproductive forms, elementary bodies (EB) and reticulate bodies (RB), respectively. The outer membrane proteins of EB are highly cross-linked with disulfide bonds. The chlamydial outer membrane complex (COMC), which includes the major outer membrane protein (MOMP), is a major component of the chlamydial outer membrane. The COMC is made up of a number of cysteine-rich proteins (Everett et al. (1995) *J. Bacteriol.* 177:877–882; Newhall et al. (1986) *Infect. Immun.* 55:162–168; Sardinia et al. (1988) *J. Gen. Microbiol.* 134:997–1004), as determined by the insolubility of proteins in the weak anionic detergent N-lauryl sarcosinate (Sarkosyl). Insolublity of proteins in Sarkosyl is a characteristic of integral outer membrane proteins of gram-negative bacteria (Filip et al. (1973) *J. Bacteriol.* 115:717–722). The COMC is present on the outer membrane proteins of EB, but not of RB. In contrast, MOMP is present throughout the developmental cycle in both EB and RB and is thought to have a structural role due to its predominance and extensive disulfide crosslinking in the EB membrane. Another function of MOMP is as a porin which allows for non-specific diffusion of small molecules into *Chlamydia* (Bavoil et al. (1984) *Infect. Immun.* 44:479–485, Wyllie et al. (1998) *Infect. Immun.* 66:5202–5207).

As with many pathogens, the development of a vaccine to *Chlamydia* has proven difficult. Much of the focus for a vaccine candidate has been on the chlamydial major outer membrane protein (MOMP) (see, e.g., U.S. Pat. Nos. 5,770,714 and 5,821,055; and PCT publication nos. WO 98/10789; WO 99/10005); WO 97/41889 (describing fusion proteins with MOMP polypeptides); WO 98/02546 (describing DNA immunization based on MOMP-encoding sequences); WO 94/06827 (describing synthetic peptide vaccines based on MOMP sequences); WO 96/31236). MOMP has been estimated to make up over 60% of the total outer membrane of *Chlamydia* and is an exposed surface antigen (Caldwell et al. (1981) *Infect. Immun.* 31:1161–1176) with different sequence regions conferring serotype, serogroup and species reactivities (Stephens et al. (1988) *J. Exp. Med.* 167:817–831). The protein consists of five conserved segments and four variable segments with the variable segments corresponding to surface exposed regions and conferring serologic specificity (Stephens et al. (1988) *J. Exp. Med.* 167:817–831). It has been suggested that these variable segments provide *Chlamydia* with antigenic variation, which in turn is important in evading the host immune response (Stephens, 1989 Antigenic variation of *Chlamydia trachomatis*, p. 51–62. In J. W. Moulder (ed.), Intracellular Parasitism. CRC Press, Boca Raton.). A potential problem in making a vaccine to an antigenically variant region is that a vaccine to one region of MOMP may only confer protection to that serovar. Also, making a subunit vaccine to an antigenic variable region may prove difficult since conformational antigenic determinants may be essential to elicit effective immunization (Fan et al. (1997) *J. Infect. Dis.* 176:713–721). Although the use of MOMP as a vaccine still seems promising, these potential problems strongly suggest that other vaccine targets should be explored.

Other proposed *Chlamydia* vaccine targets have been described and include, for example, glycolipid exoantigen (see, e.g., U.S. Pat. Nos. 5,840,297; 5,716,793 and 5,656, 271). Other *Chlamydia* vaccines have used other proteins (see, e.g, PCT publication no. WO 98/58953, describing a surface protein of *C. pneumoniae*) or a cocktail of proteins (see, e.g., U.S. Pat. Nos. 5,725,863; and 5,242,686) or have used live or attenuated whole bacteria (see, e.g. U.S. Pat. Nos. 5,972,350; 4,267,170; and 4,271,146). The sequencing of the genome of *C. trachomatis* has provided a tool to identify candidate vaccine targets (Stephens et al. (1998) *Science* 282:754–759) and examination of antibodies present in serum of infected individuals (Sanchez-Campillo et al. (1999) *Electrophoresis* 20:2269–79) have provided tools for the identification of additional vaccine targets.

There is a need in the field for the development of chemotherapeutics and vaccines that provide protection against *Chlamydia* and *Chlamydiophila* infection. The present invention addresses these needs.

SUMMARY OF THE INVENTION

The present invention features the use of PorB polypeptide as a therapeutic agent. In specific embodiment the invention features a chlamydial vaccine based on a PorB polypeptide, as well as methods for induction of a protective immune response against infection by *Chlamydia* and *Chlamydiophila*. The invention further features methods for identifying agents that offset PorB function (e.g., in transport of α-ketoglutarate and which are effective as anti-chlamydial chemotherapeutic agents.

BRIEF DESCRIPTION OF THE DRAWINGS

FIG. 1 is an alignment of the amino acid sequences of PorB (SEQ ID NO:2) and MOMP (SEQ ID NO:3).

DETAILED DESCRIPTION OF PREFERRED EMBODIMENTS

Figure 2:
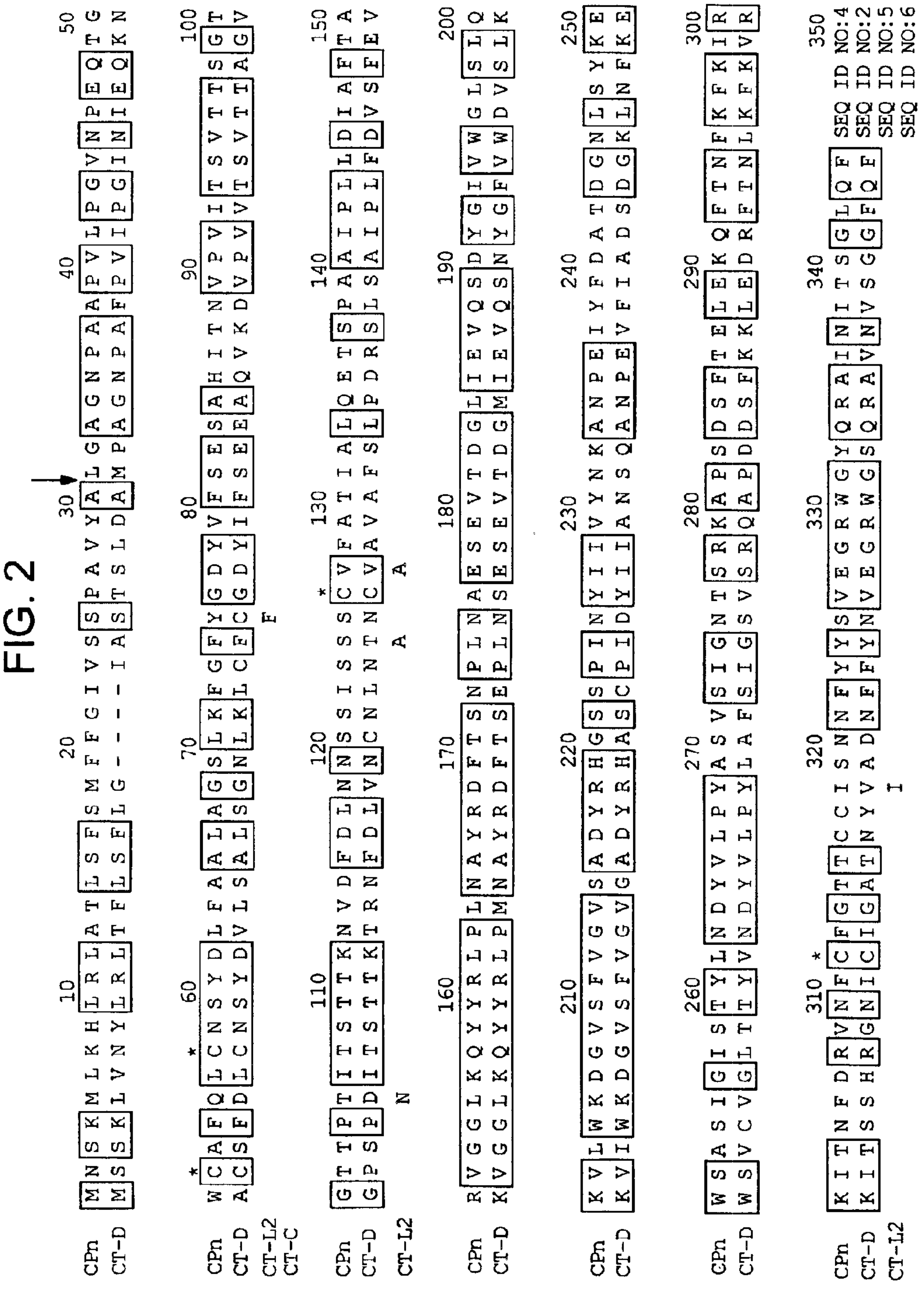
FIG. 2 is a schematic showing the alignment of the amino acid sequences of PorB from *C. trachomatis* serovars D (CT-D) (SEQ ID NO:2), L2 (CT-L2) (SEQ ID NO:5), and C (CT-C) (SEQ ID NO:6), as well as the amino acid sequence of PorB from *C. pneumoniae* (CPn) (SEQ ID NO:4). *C. trachomatis* serovar L2 and C differences are indicated below the amino acid sequence. The cysteines are indicated with an asterisk above the amino acid sequence.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of such cells and reference to "the polynucleotide" includes reference to one or more polynucleotides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

As used herein, "immunoprotective response" is meant to encompass humoral and/or cellular immune responses that are sufficient to: 1) inhibit or prevent infection by a microbial organism, particularly a pathogenic microbial organism; and/or 2) prevent onset of disease, reduce the risk of onset of disease, or reduce the severity of disease symptoms caused by infection by a microbial organism, particularly a pathogenic microbial organism.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, preferably 75% free, and most preferably 90% free from other components with which it is naturally associated.

The term "artificial membrane" is meant to encompass a membrane that provides for incorporation of a functional PorB in the membrane (e.g. a PorB that can transport α-ketoglutarate), but which is not a part of a living organism (e.g., a liposome, a lipid bilayer that is formed in vitro and independent of a living cell, and the like).

By "subject" or "patient" or "individual" is meant any mammalian subject for whom diagnosis or therapy is desired, particularly humans. Other subjects may include cattle, sheep (e.g., in detection of sheep at risk of abortion due to chlamydial infection), dogs, cats (e.g., in detection of cats having eye and/or respiratory infections), birds (e.g. chickens or other poultry), guinea pigs, rabbits, rats, mice, horses, and so on. Of particular interest are subjects having or susceptible to *Chlamydia* infection, particularly to infection by *C. trachomatis, C. psittaci* and/or *C. pneumoniae.*

The term "effective amount" or "therapeutically effective amount" means a dosage sufficient to provide for treatment for the disease state being treated or to otherwise provide the desired effect (e.g., induction of an effective immune response or reduction of bacterial load). The precise dosage will vary according to a variety of factors such as subject-dependent variables (e.g., age, immune system health, etc.), the disease (e.g., the species of the infecting pathogen), and the treatment being effected. In the case of an intracellular pathogen infection, an "effective amount" is that amount necessary to substantially improve the likelihood of treating the infection, in particular that amount which improves the likelihood of successfully preventing infection or eliminating infection when it has occurred.

"Treatment" or "treating" as used herein means any therapeutic intervention in a subject, usually a mammalian subject, generally a human subject, including: (i) prevention, that is, causing the clinical symptoms not to develop, e.g, preventing infection and/or preventing progression to a harmful state; (ii) inhibition, that is, arresting the development or further development of clinical, symptoms, e.g., mitigating or completely inhibiting an active (ongoing) infection so that bacterial load is decreased to the degree that it is no longer seriously harmful, which decrease can include complete elimination of an infectious dose of a *Chlamydia* bacteria from the subject; and/or (iii) relief, that is, causing the regression of clinical symptoms, e.g., causing a relief of fever, inflammation, and/or other symptoms caused by an infection.

As a point of clarification, it is noted that recently two species of bacterium, *Chlamydia psittacci* and *Chlamydia pneumoniae*, have been reclassified into the genus *Chlamydophila.* Unless specifically noted otherwise, reference to the genus *Chlamydia* is meant to encompass all bacteria belonging to this genus, as well as the *psittacci* and *pneumoniae* species that have or soon may be reclassified as *Chlamydophila*. Use of the terms "*Chlamydia*" and "chlamydial" are not meant to be limiting to those bacterial species originally classified *Chlamydia*, but are also meant to encompass the newly classified species of *Chlamydophila* as well unless specifically noted otherwise.

Overview

The invention is based on the expression and characterization of a chlamydial outer membrane porin protein, PorB, of *C. trachomatis*, and the further discovery that anti-PorB antibodies neutralizes the infectivity of *Chlamydia.*

The inventors have discovered that PorB has several characteristics that make it an effective vaccine and chemotherapeutic target. Unlike other vaccine candidates such as MOMP, PorB does not vary substantially in its amino acid sequence between serovars and was instead highly conserved among the *C. trachomatis* strains tested. This lack of variable regions indicates that PorB does not participate in antigenic variation that contributes to invasion of the immune response. PorB sequences between *C. trachomatis* and *C. pneumoniae* are also conserved further supporting a requirement for constrained sequence to ensure its specific function, and providing further evidence that a vaccine based on a PorB polypeptide from one chlamydial species can provide for immunoprotection across chlamydial species.

In addition, PorB facilitate transport of α-ketoglutarate into the chlamydial bacterium. α-ketoglutarate feeds the chlamydial tricarboxylic acid (TCA) cycle, and is essential for providing the bacterium with carbon and energy production intermediates. Blocking of PorB function, then can lead to arrest of bacterial cell growth and/or cell death. Thus, PorB is an attractive chemotherapeutic target.

The invention thus provides vaccines based upon PorB, and methods of inducing anti-chlamydial immunity based on these vaccines. In addition, the invention also provides for detection of PorB polypeptides or PorB-encoding sequences in diagnosis of *Chlamydia* infection.

The invention further features methods of identifying anti-chlamydial chemotherapeutics based upon identification of agents that inhibit PorB function in α-ketoglutarate transport.

Specific aspects of the invention will now be described in more detail.

Vaccines

In one aspect, the present invention provides a method of inducing a protective immune response to infection by *Chlamydia* by use of a vaccine composition comprising an immunogenic PorB polypeptide.

The PorB polypeptide delivered to the host to elicit an immune response may be a complete (e.g., native or full-length) PorB polypeptide protein, or an immunoprotective portion (i.e., a portion of the PorB polypeptide sufficient to elicit a protective immune response) thereof. The PorB polypeptide can be the naturally-occurring form of the protein, or an immunogenic, immunoprotective fragment thereof (i.e., a fragment of PorB polypeptide that, upon administration to a host, can elicit an immune response, preferably an immunoprotective immune response), a recombinant form of PorB polypeptide, a synthetically produced PorB polypeptide or immunogenic fragment thereof, a modified recombinant PorB polypeptide (e g, PorB polypeptide provided as a fusion protein), a PorB polypeptide variant or analog that retains immunogenicity of native PorB or an immunogenic fragment thereof (e.g. an immunogenically similar or identical PorB-derived amino acid sequence), and the like. PorB polypeptide fragments of interest are generally from at least about 6 amino acids to about fragments of about 8 amino acids, usually at least about 12 amino acids, more usually at least about 20 amino acids, and generally at least about 50 to 100 amino acids.

In one embodiment, the vaccine comprises a PorB polypeptide of *C. trachomatis, C. pneumoniae* or *C. psittaci*, preferably a PorB polypeptide of *C. trachomatis*. In one embodiment the *C. trachomatis* polypeptide comprises an amino acid sequence of an immunogenic fragment of SEQ ID NO:2.

PorB polypeptide can be delivered to the host in a variety of ways including, but not limited to, delivery as an isolated or substantially purified protein preparation, by immunization with a PorB polypeptide-encoding nucleic acid (e.g., by genetic immunization techniques known in the art), or by delivery of shuttle vector (e.g., a viral vector (e.g., a recombinant adenoviral vector), a recombinant bacterial vector (e.g., a live, attenuated heterologous bacterial strain, e.g., live, attenuated Salmonella) that provides for delivery of PorB polypeptide-encoding nucleic acid for expression in a host cell. Where nucleic acid encoding a PorB polypeptide is used in the vaccine formulation, the nucleic acid (e.g., DNA or RNA) can be operably linked to a promoter for expression in a cell of the subject.

Formulation of Vaccine

The PorB polypeptide-based vaccine can be formulated in a variety of ways. In general, the vaccine of the invention is formulated according to methods well known in the art using suitable pharmaceutical carrier(s) and/or vehicle(s). A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, a vaccinal composition of the invention may be formulated to contain other components, including, e.g., adjuvants, stabilizers, pH adjusters, preservatives and the like. Such components are well known to those of skill in the vaccine art.

Administration of Vaccine

The PorB polypeptide vaccine is administered in an "effective amount," that is, an amount of PorB polypeptide or PorB polypeptide-encoding nucleic acid that is effective in a route of administration to elicit an immune response effective to facilitate protection of the host against infection by *Chlamydia*. For example, where PorB polypeptide is delivered using a nucleic acid construct or a recombinant virus, the nucleic acid construct or recombinant virus is administered in an amount effective for expression of sufficient levels of the selected gene product to provide a vaccinal benefit, i.e., protective immunity.

Conventional and pharmaceutically acceptable routes of administration include intranasal, intramuscular, intratracheal, subcutaneous, transdermal, subdermal, intradermal, topical, rectal, oral and other parental routes of administration. Routes of administration may be combined, if desired, or adjusted depending upon the immunogen or the disease. The vaccine composition can be administered in a single dose or in multiple doses, and may encompass administration of booster doses, to elicit and/or maintain immunity. Methods and devices for accomplishing delivery are well known in the art. For example for administration through the skin, any of a variety of transdermal patches can be used to accomplish delivery.

The amount of PorB polypeptide, PorB polypeptide-encoding nucleic acid, or PorB polypeptide recombinant virions in each vaccine dose is selected as an amount which induces an immunoprotective response without significant, adverse side effects in typical vaccines. Such amount will vary depending upon which specific immunogen is employed, whether or not the vaccine is adjuvanted, and a variety of host-dependent factors. Where PorB polypeptide protein is delivered directly, it is expected that each does will comprise 1–1000 $\mu$g of protein, generally from about 1–200 $\mu$g, normally from about 10–100 $\mu$g. An effective dose of a PorB nucleic acid-based vaccine will generally involve administration of from about 1–1000 $\mu$g of nucleic acid. An optimal amount for a particular vaccine can be ascertained by standard studies involving observation of antibody titres and other responses in subjects. The levels of immunity provided by the vaccine can be monitored to determine the need, if any, for boosters. Following an assessment of antibody titers in the serum, optional booster immunizations may be desired. The immune response to the protein of this invention is enhanced by the use of adjuvant and or an immunostimulant.

Subjects

Using the methods and compositions described herein in connection with the subject invention, an immunoprotective response against chlamydial infection can be induced in any subject, human or non-human, susceptible to infection by a chlamydial strain, particularly a chlamydial strain pathogenic for the subject species. In general, the methods of the invention are effective in preventing or inhibiting infection of a *Chlamydia* species that expresses on its surface a protein that is immunocrossreactive with PorB. In one embodiment administration of a PorB polypeptide of *C. trachomatis* induces an immune response protective against infection by *C. trachomatis, C. pneumoniae* and *C. psittaci*, particularly an immunoprotective response against *C. trachomatis*. In another embodiment administration of a PorB polypeptide of *C. pneumoniae* induces a protective immune response against infection by *C. trachomatis, C. pneumoniae* and *C. psittaci*, and particularly an immunoprotective response against *C. pneumoniae*. In another embodiment, administration of a PorB polypeptide of *C. psittaci* induces a protective immune response against infection by *C. trachomatis, C. pneumoniae* and *C. psittaci* and particularly an immunoprotective response against *C. psittaci*.

Human disease associated with chlamydial infection that can be mitigated or prevented using the methods and compositions described herein include, but are not necessarily limited to, sexually transmitted disease (urethritis and epidiymitis in men; pelvic inflammatory disease in women), conjunctivitis, and pneumonia Of particular interest is the inhibition or prevention of infection by *C. trachomatis*, by C. *pneumonia*, and by *C. psittaci*. Exemplary chlamydial diseases are described in more detail below.

*C. trachomatis*, the most common cause of sexually transmitted diseases in the United States, causes a variety of diseases including nongonococcal urethritis and epididymitis in men; cervicitis, urethritis, and pelvic inflammatory disease in women; Reiter's syndrome; and neonatal conjunctivitis and pneumonia, the latter of which are generally acquired through maternal transmission. *C. trachomatis* has been implicated in 20% of adults with pharyngitis. Several immunotypes of *C. trachomatis* can cause lymphogranuloma venereum (LGV), a disease found mostly in tropical and subtropical areas. LGV strains invade and reproduce in regional lymph nodes.

*C. pneumoniae* (previously called Taiwan acute respiratory agent or TWAR), originally considered a serotype of *C. psittaci*, can cause pneumonia, especially in children and young adults. The organism has been found in atheromatous lesions, and infection is associated with increased risk of coronary artery disease.

*C. psittaci* infects many animals, but human infection is closely related to contact with birds. In humans, *C. psittaci* causes psittacosis, an infectious a typical pneumonia transmitted to humans by certain birds. In humans, psittacosis (ornithosis, parrot fever) is usually caused by inhaling dust from feathers or excreta of infected birds or by being bitten by an infected bird; rarely, it occurs by inhaling cough droplets of infected patients or venereally. Human-to-human transmission may be associated with highly virulent avian strains.

Where the subject is non-human, subjects of particular interest include feline, bovine, and avian subjects.

Anti-PorB Antibodies

Antibodies that specifically bind a PorB polypeptide can be administered to provide temporary, passive immunity against chlamydial infections. Methods for production of anti-PorB antibodies (e.g., monoclonal-or polyclonal antibodies) are well known in the art, as are methods for formulating such antibodies for administration. In one embodiment the anti-PorB antibody is a humanized antibody. Anti-PorB antibodies of interest also encompass modified antibodies (e.g., modified to increase biological half-life following administration).

Anti-PorB antibodies are administered in an amount sufficient to neutralize *Chlamydia* so as to prevent, mitigate, or reduce the likelihood of onset of infection. Anti-PorB antibodies can be administered by any suitable route, generally by parenteral injection (e.g. subcutaneous, intramuscular, intravenous, etc.). Administration of anti-PorB antibodies particularly useful for preventing or inhibiting infection in immunocompromised subjects or other subjects having an immune system that can not maintain an effective, immunoprotective response to, for example, a PorB antigen.

Antibodies that bind PorB of two or more Chliamydial species in a manner effective to block infection by each of these species are of particular interest. For example, antibodies that bind PorB of *C. trachomatis* as well as PorB of *C. pneumoniae* and/or *C. psittaci*, can be used to provide passive immunity that protects against infection by each of these chlamydial species.

Diagnosis of Chlamydial Infection

In addition to the uses in vaccines described above, PorB polypeptides and sequences obtained from PorB-encoding polynucleotides can be used in the detection of *Chlamydia* infection in a subject and/or determining whether a subject has been exposed to *Chlamydia* infection. Diagnostic assays based upon detection of PorB or a PorB-encoding sequence in a biological sample include, but are not necessarily limited to, detection of PorB polypeptides, detection of anti-PorB antibodies, and/or detection of PorB-encoding sequences in a test sample from the subject. Detection of any of these PorB polypeptide, polynucleotides, or antibodies in a sample taken from a subject is indicative of chlamydial infection in the subject. For clarity, applicants note that "probe" as used herein in the context of detection of PorB polypeptides or PorB polypeptide-encoding polynucleotides is meant to encompass anti-PorB antibodies (e.g. for detection of PorB polypeptide), PorB polypeptide or fragments thereof (e.g., for detection of anti-PorB antibodies), and PorB polynucleotides and fragments thereof (e.g., for use in hybridization or PCR assays to detect PorB polynucleotides).

In one general embodiment, the methods of the invention involves detecting PorB polypeptides or anti-PorB antibodies in the subject by contacting an appropriate biological test sample from a subject suspected having been exposed to *Chlamydia* or suspected of having a *Chlamydia* infection with a probe that is one of a) an antibody that specifically binds a PorB polypeptide, b) a PorB polypeptide. After the test sample is contacted with the probe for a time sufficient to allow for formation of specific antibody-PorB polypeptide binding pairs, the formation of such binding pairs is detected. Detection of the antibody-PorB binding pairs indicates that the subject has been exposed to *Chlamydia* (due to the presence of PorB polypeptides in the sample where the probe is an anti-PorB antibody), or has mounted an immune response to PorB polypeptide (due to the presence of anti-PorB antibodies in the sample, as detected using a PorB polypeptide probe) which suggests at least prior exposure to *Chlamydia.*

In another general embodiment, the presence of a *Chlamydia* infection in the host is detected using an probe to specifically hybridizes to and/or specifically amplifies (e.g. through use of PCR) to a PorB polypeptide encoding polynucleotide. Detection of hybridization or detection of a specific PCR product indicates that the subject has a *Chlamydia* infection.

Diagnosis Based on Detection of PorB Polypeptides and/or anti-PorB Antibodies

Detection of PorB polypeptides can be accomplished according to a wide variety of immunoassays that are well known in the art, and may be performed either qualitatively or quantitatively. For example, the diagnostic assay can measure the reactivity between an anti-PorB antibody (e.g., a polyclonal or monoclonal antibody (MAb), preferably a MAb) and a patient sample, usually a sample of a bodily fluid, e.g., mucosal secretion, blood-derived sample (e.g., plasma or serum), urine, and the like. The patient sample may be used directly, or diluted as appropriate, usually about 1:10 and usually not more than about 1:10,000. Immunoassays may be performed in any physiological buffer, e.g. PBS, normal saline, HBSS, PBS, etc.

In one embodiment, a conventional sandwich type assay is used. A sandwich assay is performed by first immobilizing proteins from the test sample on an insoluble surface or support. The test sample may be bound to the surface by any convenient means, depending upon the nature of the surface, either directly or indirectly. The particular manner of binding is not crucial so long as it is compatible with the reagents and overall methods of the invention. They may be bound to the plates covalently or non-covalently, preferably non-covalently.

The insoluble supports may be any compositions to which the test sample polypeptides can be bound, which is readily separated from soluble material, and which is otherwise compatible with the overall method of detecting and/or measuring type I cell- or type II cell-specific polypeptide. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Before adding patient samples or fractions thereof, the non-specific binding sites on the insoluble support, i.e. those not occupied by polypeptide, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used.

Samples, fractions or aliquots thereof can be added to separately assayable supports (for example, separate wells of a microtiter plate). A series of standards, containing known concentrations of PorB can be assayed in parallel with the samples or aliquots thereof to serve as controls and to provide a means for quantitating the amounts of PorB polypeptide present in the test sample. Preferably, each sample and standard will be added to multiple wells so that mean values can be obtained for each.

After the test sample polypeptides are immobilized on the solid support, anti-PorB antibody is added. The incubation time of the sample and the antibody should be for at time sufficient for antibody binding to the insoluble polypeptide. Generally, from about 0.1 to 3 hr is sufficient, usually 1 hr sufficing.

After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample. After washing, antibody binding to the sample can be detected by virtue of a detectable label on the antibody. Where the antibody is not detectably labeled, antibody binding can be detected by contacting the sample with a solution containing antibody-specific second receptor, in most cases a secondary antibody (i.e., an anti-antibody). The second receptor may be any compound which binds antibodies with sufficient specificity such that the bound antibody is distinguished from other components present In a preferred embodiment, second receptors are antibodies specific for the anti-PorB antibody, and may be either monoclonal or polyclonal sera, e.g. goat anti-mouse antibody, rabbit anti-mouse antibody, etc.

The antibody-specific second receptors are preferably labeled to facilitate direct, or indirect quantification of binding. Examples of labels which permit direct measurement of second receptor binding include light-detectable labels, radiolabels (such as $^{3}H$ or $^{125}I$); fluorescers, dyes, beads, chemiluminescers, colloidal particles, and the like. Examples of labels which permit indirect measurement of binding include enzymes where the substrate may provide for a colored or fluorescent product. In a preferred embodiment, the second receptors are antibodies labeled with a covalently bound erzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

Alternatively, the second receptor may be unlabeled. In this case, a labeled second receptor-specific compound is employed which binds to the bound second receptor. Such a second receptor-specific compound can be labeled in any of the above manners. It is possible to select such compounds such that multiple compounds bind each molecule of bound second receptor. Examples of second receptor/second receptor-specific molecule pairs include antibody/anti-antibody and avidin (or streptavidin)/biotin. Since the resultant signal is thus amplified, this technique may be advantageous where only a small amount of PorB polypeptide is present, or where the background measurement (e.g., non-specific binding) is unacceptably high. An example is the use of a labeled antibody specific to the second receptor. More specifically, where the second receptor is a rabbit anti-allotypic antibody, an antibody directed against the constant region of rabbit antibodies-provides a suitable second receptor specific molecule. The anti-Ig will usually come from any source other than human, such as ovine, rodentia, particularly mouse, or bovine.

The volume, composition and concentration of anti-antibody solution provides for measurable binding to the antibody already bound to receptor. The concentration will generally be sufficient to saturate all antibody potentially bound to PorB polypeptide. The solution containing the second receptor is generally buffered in the range of about pH 6.5–9.5. The solution may also contain an innocuous protein as previously described. The incubation time should be sufficient for the labeled ligand to bind available molecules. Generally, from about 0.1 to 3 hr is sufficient, usually 1 hr sufficing.

After the second receptor or second receptor-conjugate has bound, the insoluble support is generally again washed free of non-specifically bound second receptor, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and is O-phenylenediamine which yields a colored product under appropriate reaction conditions. Appropriate substrates for other enzyme conjugates such as those disclosed above are known to those skilled in the art. Suitable reaction conditions as well as means for detecting the various usefull conjugates or their products are also known to those skilled in the art. For the product of the substrate O-phenylenediamine for example, light absorbance at 490–495 nm is conveniently measured with a spectrophotometer.

The absence or presence of antibody binding may be determined by various methods that are compatible with the detectable label used, e.g., microscopy, radiography, scintillation counting, etc. Generally the amount of bound anti-PorB antibody detected will be compared to control samples (e.g., positive controls containing PorB or negative controls lacking such polypeptides). The presence of anti-PorB antibody is indicative of the presence of a *Chlamydia* in the test sample, which in turn is indicative of chlamydial infection in the subject.

As will be readily appreciated by the ordinarily skilled artisan upon reading the present disclosure, the above techniques can be readily modified to provide for detection of anti-PorB antibodies in the host. For example, rather than immobilizing PorB polypeptide on a solid support, an anti-PorB antibody is immobilized on the support and subsequently contacted with a test sample from the host. Binding of PorB polypeptide from the test sample to the support-bound anti-PorB antibody can then be detected using a second anti-PorB antibody (e.g., that binds to a different epitope of the polypeptide than the bound antibody). Binding of the second antibody can then be detected according to methods well known in the art.

Diagnosis Based on Detection of PorB Nucleic Acid

Where the diagnostic assay involves detection of a PorB-encoding sequence, the assay can take advantage of any of a variety of polynucleotide detection techniques that are well known in the art. For example, a fragment of a PorB-encoding sequence can be used as a probe to detect hybridizing sequences in a test sample, or for use as a primer in PCR amplification of chlamydial nucleic acid in at test sample. Methods for detecting sequences based on hybridization, as well as use of PCR are known in the art, see, e.g., Sambrook, et al. Molecular Cloning: A Laboratory Manual, CSH Press 1989. The probe or primer may comprise a detectable label. Suitable labels include fluorochromes, e.g. fluorescein isothiocyanate (FITC), rhodamine, Texas Red, phycoerytirin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the polynucleotide is conjugated to biotin, haptens, etc. having a high affinity binding partner, e.g. avidin, specific antibodies, etc., where the binding partner is conjugated to a detectable label. In PCR, the label may be conjugated to one or both of the primers; alternatively, the pool of nucleotides used in the amplification is labeled, so as to incorporate the label into the amplification product.

Kits for Detection of *Chlamydia*

PorB polypeptides (for detection of specific antibodies), anti-PorB antibodies, and PorB polynucleotide probes and/or primers, as well as other materials useful in the diagnostic methods of the invention (e.g., labels, compounds for detection of labels, solid supports for capture of nucleic acid in a sample, filters for at least partial separation or purification of parasites in the sample, detergents and other reagents (e.g., lysing mammalian and cells in the sample), etc.) can be provided in a kit. Such kits can include samples to serve as positive controls or negative controls. Preferably such kits are designed for use in the field, e.g., do not contain components that require refrigeration, are portable, etc.

PorB as a Chemotherapeutic Target and Identification of Anti-Chlamydial Agents

Also of interest are candidate agents that affect PorB expression (e.g. by affecting PorB promoter function) or that interact with PorB polypeptides. Agents of interest can include those that inhibit PorB activity. PorB activity can be decreased by, for example, decreasing the efficiency of α-ketoglutarate transport by PorB, associating with the porin to inhibit α-ketoglutarate transport, decreasing transcription or translation of the PorB gene product, and the like. Agents that decrease PorB activity can be used to, for example, treat *Chlamydia* infection in a subject. The agent can be selected for chemotherapeutic activity against chlamydia either extracellularly, intracellulary, or both.

"Candidate agents" is meant to include synthetic molecules (e.g., small molecule drugs, peptides, or other synthetically produced molecules or compounds, as well as recombinantly produced gene products) as well as naturally-occurring compounds (e.g., polypeptides, factors endogenous to a prokaryotic or eukaryotic host cell, plant extracts, and the like). Of particular interest are candidate agents that can cross the cell membrane of the host cell for the treatment of intracellular bacteria.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fingal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Drug Screening Assays

In general, drug screening identifies agents that reverse or inhibit PorB function and may provide a means to treat a *Chlamydia* infection in a subject. Of particular interest are screening assays for agents that have a low toxicity for subject cells and are able to cross the cell membrane of subject cells. Generally a plurality of assay mixtures are run in parallel with different agent concentrations to obtain a differential response to the various concentrations. Typically, one of these concentrations serves as a negative control, i.e. at zero concentration or below the level of detection.

Screening of Candidate Agents in vitro

A wide variety of in vitro assays may be used to screen agents for their ability to affect PorB activity, including screening for antibacterial (e.g., bactericidal, bacteriostatic, etc.) activity in a chlamydial culture (e.g., in an infected cell line, etc.), labeled in vitro binding assays (e.g., competitive binding assays, and the like), immunoassays for protein binding, liposome-swelling assays (e.g., liposomes having incorporated PorB), and the like. For example, by providing for the production of large amounts of PorB protein, one can identify ligands or substrates that bind to the protein. The purified protein may also be used for determination of three-dimensional crystal structure, which can be used for modeling intermolecular interactions (e.g. to model interaction of the porin with α-ketoglutarate to provide the basis of rational drug design).

The screening assay can be a binding assay, wherein one or more of the molecules may be joined to a label, and the label directly or indirectly provides a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assays described herein. Where the assay is a binding assay, these include reagents like salts, neutral proteins, e.g. albumin, detergents, etc that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

PorB-encoding nucleic acid can be introduced and expressed in a prokaryotic recombinant host cell (e.g., *E. coli*, and the like) so to provide for production of functional PorB in the bacterial outer membrane. The PorB-expressing recombinant host cell can then be contacted with candidate agents and control substrates known to diffuse through PorB, e.g. α-ketoglutarate, succinate, oxaloacetate, arabinose, glucose, glutamate, adipate, malonate, etc., preferably α-ketoglutarate, and the effect of the candidate agent on PorB function in transport of the control substances tested. For example, the candidate agent or the control substance can be detectably labeled, and the effect of the candidate agent monitored by means of the detectable label. For example, wherein the control substrate is detectably labeled, the ability of the candidate agent to inhibit PorB transport of the control substrate can be monitored by examining depletion of the detectable label from the extracellular media or by examining the level of intracellular detectable label, or both.

In one embodiment, the ability of an agent to modulate PorB function is evaluated using PorB within an artificial membrane. In one example, the artificial membrane is provided in the context of a liposome. In a specific embodiment, the assay is based on a liposome swelling assay (see, e.g., Nikaido (1983) *Methods Enzymol.* 97:85–95; Nikaido and Rosenberg (1983) *J. Bacteriol.* 153:241–252). Briefly, PorB is cloned and expressed in a suitable cell line, e.g. *E. coli.*, purified, and incorporated into liposomes. The liposomes can then be contacted with candidate agents and control substrates known to diffuse through PorB, e.g. α-ketoglutarate, succinate, oxaloacetate, arabinose, glucose, glutamate, adipate, malonate, etc., and liposome swelling measured, for example, by following the change in $O.D._{400}$ using a Perkin-Elmer spectrophotometer and an attached chart recorder. Altered liposome swelling as compared to a control liposome contacted with only the substrate indicates that the candidate agent can modulate PorB function. Of particular interest are agents that inhibit PorB function as evidenced by reduced liposome swelling as compared to a control.

The screening assays of the invention can be supplemented by, or modified to, identify agents that can enter into an infected eukaryotic cell, where it can exhibit its anti-chlamydial effect upon intracellular bacteria. This can be accomplished by, for example, contacting candidate agents, particularly those pre-screened for their inhibition of PorB function, with mammalian cells infected with chlamydia, and assessing the effect of the agent upon growth of the intracellular bacteria (e.g., by assessing affect upon growth rate, bacterial load in the host cell, and the like).

Other variations on the screening assay to identify agents that affect PorB function are within the scope of the present invention. For example, a polynucleotide encoding PorB or a modified PorB polypeptide (e.g., PorB fusion polypeptide or other modified PorB polypeptide that is adapted for expression in and insertion into the extracellular membrane of a eukaryotic host cell) can be introduced into a eukaryotic (e.g., mammalian) host cell (e.g. in an isolated cell in vitro, is e.g., in a mammalian cell line) for expression using methods well known in the art. Recombinant mammalian cells producing PorB can then be screened for function in transport of the natural ligand (e.g., α-ketoglutarate) and used as the basis of an assay to identify agents that inhibit α-ketoglutarate transport.

Identified Candidate Agents

The compounds having the desired pharmacological activity may be administered in a physiologically acceptable carrier to a host for treatment of a disease associated with *Chlamydia* infection, e.g. sexually transmitted diseases, conjunctivitis, pneumonia, etc. The therapeutic agents may be administered in a variety of ways, orally, topically, parenterally e.g. subcutaneously, intraperitoneally, intravascularly, etc. Inhaled treatments are also of interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing Agents, wetting and emulsifying Agents, salts for varying the osmotic pressure or buffers for securing an adequate pH value, and skin penetration enhancers can be used as auxiliary agents.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following procedures are used in the Examples described in detail below. Although some of the methods described below are in common use, the specific protocol used in the Examples below is described in detail where alternative protocols are often employed. Basic procedures such as DNA digestion by restriction enzymes and ligation are not described, as such are well within the skill of the ordinarily skilled artisan and, in some instances, are carried out according to the enzyme or kit manufacturer's instructions.

Chlamydial cultures. *C. trachomatis* strains B/TW-5/OT, C/TW-3/OT, and L2/434/Bu were grown in L929 cells, and strain D/UW-3/Cx was grown in HeLa 229 cells. Elementary bodies (EB) and reticulate bodies (RB) were separately purified by diatrizoate (Renograffin; E. R. Squibb and Sons, Princeton, N.J.) gradients and were used immediately after purification or stored at −70 C. RB was purified at 24 hours post-infection.

Bacterial strains and plasmid. The synthetic gene encoding MOMP (ompA) was constructed in *E. coli* HMS 174 (DE3) and has been previously described (Jones et al. (2000) *Gene* 258:173–181). *E. coli* HMS 174 (DE3) without the plasmid was used as a control strain. PorB cloning and expression were done in the *E. coli* strain, TOP10 (Invitrogen, Carlsbad, Calif.). The complete PorB gene was cloned into the pBAD-TOPO TA vector (Invitrogen), which contains the araBAD promoter.

Expression and purification of PorB. Regulation of expression is by the AraC gene product on the promoter in the absence or presence of arabinose. All *E. coli* cultures were grown with aeration at 37° C. in Luria-Bertani broth containing 100 mg/ml of ampicillin until the cultures reached an O.D of 0.6. 0.02% Arabinose to a final concentration of 0.5 mM was added to induce the expression of PorB. PorB was cloned with a C-terminal HIS tag and purified by nickel column using the HIS Bind Purification system (Novagen, Madison, Wis.). Extraction of PorB with 1% octylglucoside at 37° C. for 1 h and dialysis of the detergent out of the extracted PorB using PBS and then 1× Bind buffer (Novagen) was necessary before purification by nickel column. IPTG was added to a final concentration of 0.5 mM to induce the expression of MOMP. The outer membranes of *E. coli* expressing MOMP were purified as described in MOMP Jones et al. (2000 *Gene* 258:173–181)

Outer membrane preparation. The spheroplasts and outer membranes of *E. coli* were isolated using the method of Osborn and Munson (1974 *Methods Enzymol.* 0.31:642–653) with the following modifications. The *E. coli* were grown in Luria Bertani broth with 100 mg/ml ampicillin at 37° C. with vigorous aeration to a density of approximately $5\times10^8$ bacteria/ml, followed by 2 hours of induction by addition of 0.02% arabinose to a concentration of 0.5 mM. 25 ml aliquots of the spheroplasts were lysed by sonication by immersing in an ice-salt bath and sonicating for three 15-second periods with a Braunsonic U sonicator. The suspension was cooled for 1 minute between bursts. The unbroken cells were removed by centrifugation at 1200× g for 15 minutes at 4° C. The supernatant fraction was then centrifuged for 2 hours at 100,000× g at 4° C. The membrane pellet was resuspended in a small volume of cold 0.25 M sucrose-3.3 mM Tris-1 mM EDTA, pH 7.8 and centrifuged for 2 hours at 100,000× g 4° C. The pellet was then suspended in 6 ml of cold 25% sucrose-5 mM EDTA, pH 7.5 for separation by isopycnic centrifugation. An outer membrane preparation was performed with a control clone expressing a non-outer membrane protein and this protein was not detected in the outer membrane fraction.

Chlamydial outer membrane complex (COMC) preparation. The COMC was prepared from fresh, not previously frozen, purified EB (10 mg) and performed according to the method of Caldwell et al. (Caldwell et al. (1981) *Infect. Immun.* 31:1161–1176) with some modifications. EB were suspended in 3 ml of 10 mM sodium phosphate buffer (pH 7.4) and 2% Sarkosyl. This suspension was sonicated briefly and centrfuged at 100,000× g for 1 hour at 20° C. Both the soluble and insoluble (COMC) fractions were analyzed by SDS-PAGE.

Antibodies. Polyvalent monospecific antisera to PorB were obtained from mice Swiss-Webster mice immunized with 1) nickel column-purified PorB protein and 2) a piece of PorB consisting of the amino-terminal portion, from amino acid 24–71 ($PorB^{24-71}$). The mice were immunized twice at two-week intervals with 100 μg of purified protein in an equal volume of complete Freund's adjuvant for the second immunization. IH5 is a L2 serovar specific monoclonal antibody specific to MOMP. Polyvalent antiserum produced in rabbits using L2 EB and polyvalent monospecific antiserum produced in rabbits using cloned and expressed 28 kDa plasmid protein (pgp3) (Comanducci et al. (1993) *J. Gen. Microbiol.* 139:1083–1092) were used in the dot blot experiment.

Cell staining. *C. trachomatis* serovar L2-infected, D-infected and uninfected HeLa cells were fixed in methanol for 10 minutes and washed three times in PBS. The anti-PorB monospecific antibody was diluted 1:200, added to the cells and incubated for 1 hour at room temperature on a rocker platform. The monolayer was rinsed three times in PBS and overlaid with a fluorescein isothiocyanate-conjugated anti-mouse immunoglobulin G (Zymed, So. San Francisco, Calif.) diluted 1:50. The cells were incubated in the dark for one hour at room temperature on a rocker platform and then washed three times with PBS. The cells were then counter stained with Evans blue and observed by fluorescence microscopy.

Dot Blot assay. Dot blots were performed as previously described by Zhang et al., (1987 *J. Immunol.* 138:575–581) with the following differences: 1) the method of detection was enhanced chemiluminescence (ECL) (Amersham Pharmacia Biotech, Piscataway, N.J.); 2) an anti-mouse HRP-conjugated secondary antibody was used; 3) the primary and secondary antibodies were washed by rinsing the wells with PBS and discarding the PBS. Vacuum filtration was used after the final wash to remove all liquid from the wells.

Dot blots of viable chlamydial EB to determine surface accessibility of PorB were performed by probing immobilized EB with (1) a negative control antibody, anti-pgp3; (2) a positive control monoclonal, IH5; (3) an anti-PorB antibody; (4) an anti-$PorB^{24-71}$ antibody; and (5) a positive control polyclonal, anti-L2 EB was used. The anti-pgp3 antibody was used at 1:1000 for the immunoblot and bound a 28 kDa protein, while it was used at 1:100 for the dot blot. The rabbit anti-L2 EB polyclonal antibody was used at 1:1000 for both the immunoblot and dot blot. The IH5 monoclonal antibody was used at 1:1000 for the immunoblot and at 1:4000 for the dot blot. The anti-PorB antibody was used at 1:200 for the immunoblot and at 1:100 for the dot blot.

Protease cleavage. Fresh EB, not previously frozen, were incubated with various concentrations of trypsin (0, 0.001, 0.01, 0.1 mg/ml) and proteinase K (0, 0.1, 0.5, 1 mg/ml) for 30 minutes at 37° C. The treated EB were then immediately transferred to a nitrocellulose membrane and a dot blot analysis was performed as described above.

Neutralization assay. The HaK (hamster kidney cells) in vitro neutralization assay was performed as previously described (Byrne et al. (1993) *J. Infect. Dis.* 168:415–20). Antibodies, except for pre-immune serum, were quantitated and diluted to 200 mg/ml, then serially diluted by two-fold to 12.5 mg/ml. Pre-immune serum was used at a dilution of 1:10 and serially diluted 2-fold to 1:160. For detection of PorB, monospecific anti-PorB was purified with protein A (Sigma, St. Louis, Mo.), filter sterilized, quantitated using the BCA assay (Pierce, Rockford, Ill.), and diluted in SPG to the appropriate concentrations. A control monoclonal antibody with specificity for MOMP (IH5) was used. Also, a control monoclonal antibody with unrelated specificity, the anti-pgp3 antibody as well as the pre-immune serum were used as controls. L2 EB was diluted in SPG to contain $2\times10^4$ IFU/ml, 100 ml was added to each antibody dilution in total volume of 200 ml. Neutralization proceeded for 30 minutes. IFU were quantitated by counting ten fields at a magnification of 40×. A mean IFU per field was calculated and the results were shown as percent reduction in mean IFU compared with the control plates.

Quantitation of protein. Purified protein and outer membranes for use in the liposome swelling assay was quantitated according to the Lowry method. All other samples were quantitated by the BCA assay (Pierce, Rockford, Ill.).

Liposome swelling assay. The liposome swelling assay was performed according to the method of Nikaido (Nikaido & Rosenberg (1983) *J. Bacteriol.* 153:241–252) with the following modifications: 1) liposomes were made by mixing 5.0 pmol phosphatidylcholine and 0.02 μmol dicetylphosphate with outer membrane proteins or purified protein in order to increase the optical density readings to the range of 0.4–0.7 O.D., and 2) the liposome drying time was longer than 2 minutes (i.e., 5 minutes), but at a lower temperature of 37° C. Liposomes were made with either dextran T-40 (15% dextran T40 in 5 mM Tris-Cl, pH 7.5) or stachyose inside. Since stachyose is impermeable to the porins, it was used as a control to determine the isoosmotic concentration of other solutes. The concentration of stachyose which produced no swelling or shrinking of the proteoliposomes was determined to be the isoosmotic concentration. The swelling rates were determined as d(1/OD)/dt from the optical density changes between 10 and 20 seconds (Nikaido & Rosenberg (1983) *J. Bacteriol.* 153:241–252).

Liposome swelling assay for testing anions. Liposomes were made according to the method described above with a few modifications. The following was added to phosphatidylcholine and dicetylphosphate dried with PorB (6 μg): 4 mM $NAD^+$, 12 mM stachyose, 1 mM imidazole-NAD buffer pH (6.0). The test solution consisted of 1 mM Imidazole-NAD (pH 6.0), 1 mM Sodium NAD, 6 mM disodium salt of the anion to be tested (α-ketoglutarate, succinate, oxaloacetate, malate, or citrate). Control liposomes without protein were used to determine the isotonic concentration of the test solutions.

Enzyme-linked liposome swelling assay. Liposomes were made as described above with addition of 50 mM potassium phosphate, 2.5 mM $NAD^+$, 0.2 mM thiamin pyrophosphate, 1.0 mM magnesium chloride, 0.13 mM coenzyme A, 2.6 mM cysteine, and 5.0 units of α-ketoglutarate dehydrogenase. Various concentrations of α-ketoglutarate (0.001 mM-1 mM) were used as test solutes. Liposomes containing PorB (6 μg) and control liposome without protein were made with the reaction mixture, washed through a Sephadex column (S-300) equilibrated with reaction mixture without α-ketoglutarate dehydrogenase, and placed inside a cuvette. α-ketoglutarate was added to the reaction and mixed. The formation of NADH was measured by the increase in $O.D._{340}$.

Example 1

Analysis of PorB Sequence—Comparison to Major Outer Membrane Protein (MOMP)

Genome sequence analysis revealed a number of predicted outer membrane proteins (see Stephens et al. 1998 "Genome sequence of an obligate intracellular pathogen of humans: *Chlamydia trachomatis*" *Science* 282:754–759). One such predicted outer membrane protein, encoded by the predicted open reading frame CT713, was selected for analysis, and referred to herein as PorB. The nucleotide and amino acid sequences of PorB (CT713) are available within the complete sequence of the genome at GenBank Accession No. NC_000117, with the amino acid sequence at GenBank Accession No. gi|3329169. The open reading frame corresponding to PorB is the complement of nucleotide residues 3616 to 4638 of GenBank Accession No. AE001342. The nucleotide and amino acid sequences of PorB of *C. trachomatis* are provided in the Sequence Listing as SEQ ID NOS:1 and 2, respectively. Alignment of the amino acid sequence of PorB with the amino acid sequence of MOMP is provided in FIG. 1.

As illustrated in FIG. 1, PorB has only slight sequence similarity (20.4%) to MOMP. Despite this relatively low amino acid sequence similarity, PorB and MOMP do share certain characteristics and structural features. The estimated size of this protein is 38,000 daltons and the isoelectric point was calculated to be 4.9. MOMP has a molecular weight of 40,000 with an isoelectric point calculated and experimentally confirmed to be 5.0 (Bavoil et al. (1984) *Infect. Immun.* 44:479–485). PorB has a predicted cleavable leader sequence as well as an amino acid sequence which ends in phenylalanine (arrow in FIG. 2), a characteristic of many outer membrane protein (Struyvé et al. (1991) *J. Mol. Biol.* 218:141–148). Both PorB and MOMP have the same number of cysteines (9 cysteins) suggesting that PorB may be an outer membrane cysteine-rich protein analogous to, although distinct from, MOMP.

Previous reports on outer membrane proteins of *Chlamydia* have not identified this protein. The overabundance of MOMP and similarity in size and isoelectric point likely contributed in preventing earlier detection of PorB. PorB is not as predominant as MOMP by approximately 20-fold. Since PorB is similar in size to MOMP, an SDS-PAGE analysis of chlamydial outer membrane complexes can not distinguish PorB from MOMP. Also, PorB has a similar isoelectric point to MOMP, therefore a 2-D gel analysis may not separate the proteins (Bavoil et al. (1984) *Infect. Immun.* 44:479–485; Bini et al. (1996) *Electrophoresis* 17:185–190).

Example 2

Analysis of PorB Sequence—Comparison of PorB Amino Acid Sequences from Different Serovars When compared with other serovars of *C. trachomatis*, MOMP has four distinct variable segments which correspond to surface exposed regions of the protein. Serovar designations have been related to the differences in these variable segments of MOMP (Stephens et al. (1988) *J. Exp. Med.* 167:817–831). In order to determine whether this serovar variation is also characteristic for PorB, the sequence of PorB between serovars was compared.

FIG. 2 provides an alignment of the amino acid sequences of PorB from the *C. trachomatis* serovars D (CT-D) (SEQ ID NO:2), L2 (CT-L2) (SEQ ID NO:5), and C (CT-C) (SEQ ID NO:6), as well as the amino acid sequence of PorB from *C. pneumoniae* (CPn) (SEQ ID NO:4). The PorB of *C. trachomatis* and *C. pneumoniae* are 59.4% identical. *C. trachomatis* serovar L2 and C differences are indicated below the amino acid sequence. The cysteines are indicated with an asterisk above the amino acid sequence.

The nucleotide and amino acid sequence alignments between serovars D, B, C and L2 revealed no to only minor differences. There is no PorB sequence difference between serovars D and B, while there is one nucleotide difference, which results in an amino acid change, between serovars D (or B) and C. Between serovars D (or B) and L2 there are six nucleotide differences, each of which result in a difference in the encoded amino acid. The nucleotide differences occur throughout the gene and were not clustered to any region (FIG. 2). Among the serovars investigated, there are no variable segments in PorB such as there are in MOMP. Thus, sequence variation is not a phenotype for PorB.

Comparison between PorB of *C. trachomatis* (serovar D) and *C. pneumoniae* reveals greater differences dispersed throughout the gene. However, with 59.4% identity between amino acid sequences of *C. trachomatis* and *C. pneumoniae*, this protein is highly conserved between species (FIG. 2). *C. pneumoniae* PorB has 6 cysteines, four of which are conserved between species, while *C. trachomatis* serovars D, B and C have 9 conserved cysteines and serovar L2 has 8.

Example 3

Expression of PorB in *E. coli*

PorB was predicted to be in the outer membrane through a variety of protein localization programs such as PSORT (K. Nakai, Human Genome Center, Institute for Medical Science, University of Tokyo, Japan). A leader sequence cleavage site for *C. trachomatis* PorB was predicted to be at amino acid 26 (FIG. 2). The complete gene including the leader sequence was cloned into *E. coli* with a HIS tag at the C-terminal end of PorB- and expressed. The protein was affinity purified by nickel column chromatography.

PorB expressed in *E. coli* was localized to the outer membrane fraction as determined by an immunoblot using an antibody to the C-terminal HIS tag. *E. coli* porins were also detected in this outer membrane fraction by Coomassie stain. The presence of PorB was primarily localized to the outer membrane suggesting that PorB has the necessary signal(s) to be transported to the outer membrane by *E. coli.*

Example 4

Presence of PorB in Inclusions

In order to characterize PorB in *Chlamydia*, a polyclonal monospecific serum was produced to the complete purified protein. FITC cell staining experiments using the anti-PorB serum showed that this serum contained antibody that bound antigens localized to the inclusions in infected cells. Anti-PorB serum did not label uninfected control cells. Staining cells infected with serovar L2 and serovar D, 48 and 72 hours post infection, respectively with anti-PorB serum revealed punctate staining consistent with the morphology for EB and RB. This antibody staining was present at 10, 15, 20, 24, 48 hours post infection, indicating that this protein is constitutively expressed and/or present throughout the chlamydial development cycle.

Example 5

Localization of PorB to the COMC

The anti-PorB antibody bound a protein in *Chlamydia* that was similar in size to MOMP by immunoblot analysis. The amount of PorB present in EB and RB was similar. The serum also bound the purified HIS-tagged protein, which was detected by an anti-HIS antibody. Although there were only slight similarities in sequence to MOMP, testing for cross reactivity between antibodies to PorB and MOMP was performed Anti-PorB serum did not bind MOMP expressed in *E. coli*. Therefore, it is concluded that the anti-PorB sera bound PorB and did not cross react with MOMP.

In order to determine if PorB is a component of the *Chlamydia* Outer Membrane Complex (COMC), the COMC was isolated and probed with anti-PorB serum. Since the chlamydial outer membrane is highly disulfide bonded, the Sarkosyl insoluble fraction contains a number of proteins such as MOMP and other cysteine rich proteins. PorB was detected in the COMC fraction and not the soluble supernatant. Therefore, the presence of PorB in the COMC fraction demonstrates that this protein is in the chlamydial outer membrane and is disulfide linked perhaps to other COMC proteins.

Example 6

Surface Accessibility of PorB

Since PorB was predicted to be in the outer membrane, and was localized to the COMC, surface accessibility of this protein was tested. Dot blot experiments have been shown to be specific for surface accessible antigens (Zhang et al. (1987) *J. Immunol.* 138:575–581) and was used to test surface accessibility of PorB. The dot blot using the anti-PorB sera showed that this antibody bound EB. A negative control rabbit polyclonal serum to a 28 kDa plasmid protein (pgp3) was used as a negative control antibody since this protein is not present in the outer membrane of *Chlamydia* (Comanducci et al. (1993) *J. Gen. Microbiol.* 139:1083–1092). This negative control antibody did not bind EB, while a positive control antibody to a surface accessible antigen on MOMP (IH5) bound. These data demonstrate that PorB is localized to the outer membrane.

Example 7

Effect of Proteolytic Cleavage on PorB

To investigate surface exposure of PorB, purified EB were digested with proteases and proteins from EB were assessed for binding by the anti-PorB antibody. Using the dot blot method, EB were treated with various concentrations of trypsin or proteinase K, immobilized on a nitrocellulose membrane and probed with the anti-PorB antibody, as well as to antibodies to MOMP and the anti-pgp3 antibody. A reduction in binding by anti-PorB antibodies was observed for EB-digested proteins suggesting that PorB has surface accessible trypsin and proteinase K cleavage sites, and thus is an outer membrane protein.

Example 8

Neutralization of *C. trachomatis* by Anti-PorB

Figure 3:
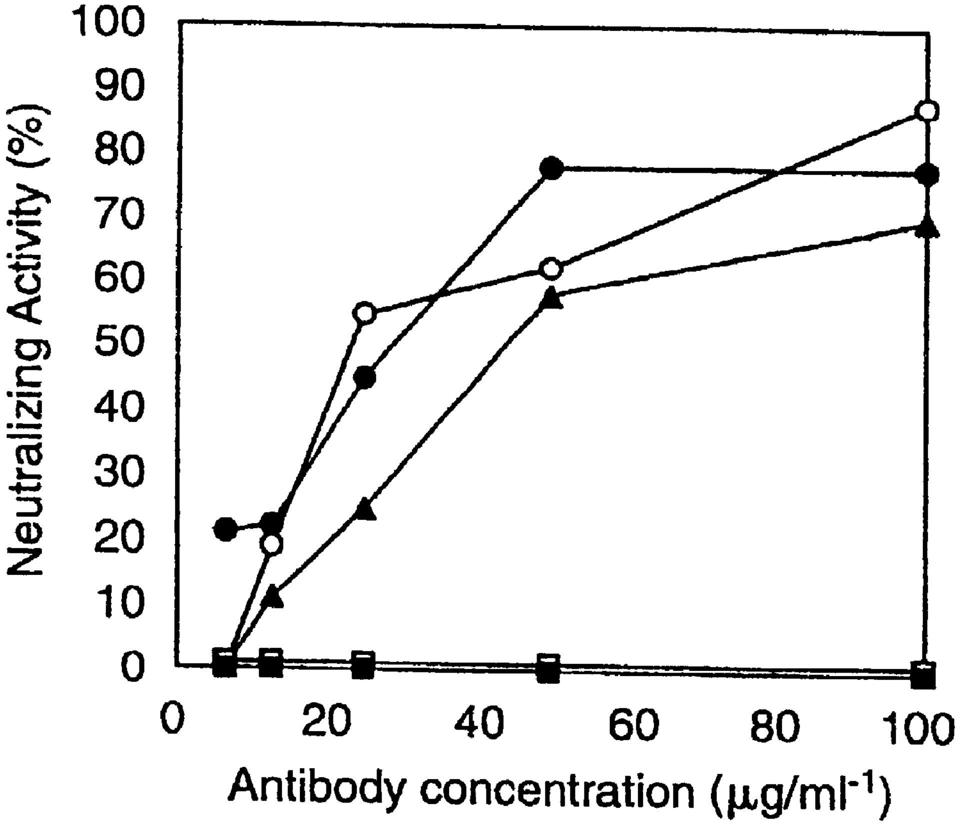
FIG. 3 is a graph showing antibody neutralization of *C. trachomatis* serovar L2 in HaK cells. Results are expressed as percentage reduction in inclusion-containing cells with respect to number of inclusion-containing cells observed after incubation with SPG only. The antibodies used were anti-PorB (open circles), anti-$PorB^{24-71}$ (closed triangles), IH5 (closed circles), anti-pgp3 (open squares) and pre-immune serum (closed squares).

Since PorB is an outer membrane protein with surface exposed regions, antibodies made to PorB were tested for ability neutralize infectivity of *C. trachomatis* (serovar L2). The anti-PorB sera produced using either the entire protein or an amino-terminal fragment (amino acids 24–71) at a concentration of 100 mg/mil neutralized infectivity by up to 88% and 70%, respectively, further supporting the conclusion that PorB is a surface exposed outer membrane protein (FIG. 3). The control antibody without specificity to outer membrane proteins, anti-pgp3, as well as the pre-immune sera did not neutralize infectivity (FIG. 3). A monoclonal antibody to serovar L2 MOMP (IH5) at a concentration of 50 and 100 mg/ml neutralized infectivity up to 78% (FIG. 3). This neutralization assay confirms that antibodies to PorB can inhibit infectivity by *C. trachomatis* since this assay is an art-recognized in vitro correlate for the assessment of protective immunity (Byrne et al. (1993) *J. Infect. Dis.* 168:415–20).

Example 9

Pore-Forming Activity of PorB

The pore-forming capabilities of PorB were tested using the liposome reconstitution assay (Nikaido (1983) *Methods Enzymol.* 97:85–95). The liposome swelling assay for study of porin function is used not only because it is well established, but because this assay gives precise information on the rates of diffusion of solutes through the porin channels (Nikaido & Rosenberg (1983) *J. Bacteriol.* 153:241–252). This assay involves the formation of liposomes incorporated with pore-forming protein and then determination of whether and how fast test solutes can diffuse through the protein channels. This assay was used to test and compare pore-forming activity of the *C. trachomatis* PorB and MOMP.

Purification of MOMP using mild detergents causes a loss in porin activity (Bavoil, et al. (1984) *Infect. Immun.* 44:479–485, Wyllie, et al. (1998) *Infect. Immun.* 66:5202–5207), therefore, MOMP was expressed in *E. coli* and outer membrane fractions enriched for MOMP were used. It has been shown in liposome swelling assays that the predominant porin activity of the outer membrane fraction of *E. coli* expressing MOMP is due to MOMP (Jones et al. (2000) *Gene* 258:173–181). This was also found to be the case for PorB except purified PorB also functioned in liposome swelling assays (FIG. 4) and was used in all subsequent experiments. To control for potential contaminants that may occur during PorB purification, another predicted outer membrane protein from *C. trachomatis* serovar D (CT241) was cloned, expressed in *E. coli* and purified by the same procedure used for PorB. Like PorB, CT241 also contains a predicted leader sequence and ends in phenylalanine and was incorporated into liposomes and tested for pore forming activity. This protein as well as liposomes without protein did not show pore-forming activity with any of the solutes tested.

Figure 4B:
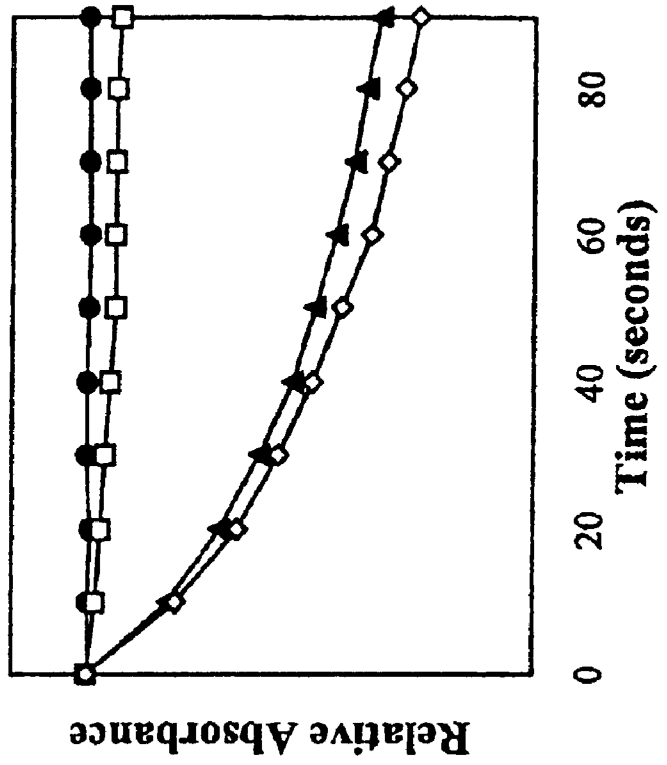
FIGS. 4A and 4B are graphs showing the results of a liposome swelling analysis of PorB (FIG. 4A) and the outer membrane of *E. coli* expressing MOMP (panel B). Liposomes were made as described and 0.017 ml out of a total of 0.3 ml was diluted in 0.6 ml of isotonic sugar solutions of stachyose (closed circles), sucrose (open squares), glucose (closed triangles) and arabinose (open circles). The y-axis represents a range of $A_{400}$ 0.15.
Figure 4A:
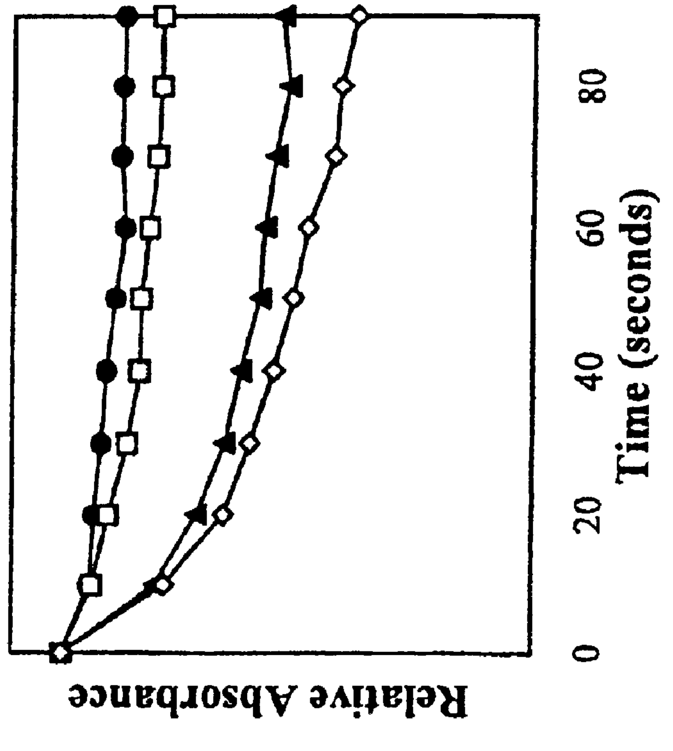

The smallest sugars tested in the liposome swelling assay were the monosaccharides arabinose and glucose. These sugars penetrated the PorB- and MOMP-containing liposomes faster than the disaccharide, sucrose, while the tetrasaccharide, stachyose, was too large to enter (FIG. 4). This diffusion selectivity of PorB- or MOMP-containing liposomes with sugars was similar to what has been observed with COMC-containing liposomes (Bavoil, et al. (1984) *Infect. Immun.* 44:479–485, Wyllie, et al. (1998) *Infect. Immun.* 66:5202–5207). Larger solutes enter into PorB or MOMP porin slower, suggesting that there is a size restriction of molecules that can enter via these porins. However, the liposomes containing PorB permitted the diffusion of arabinose or glucose at a slower rate than liposomes containing MOMP.

Figure 5A:
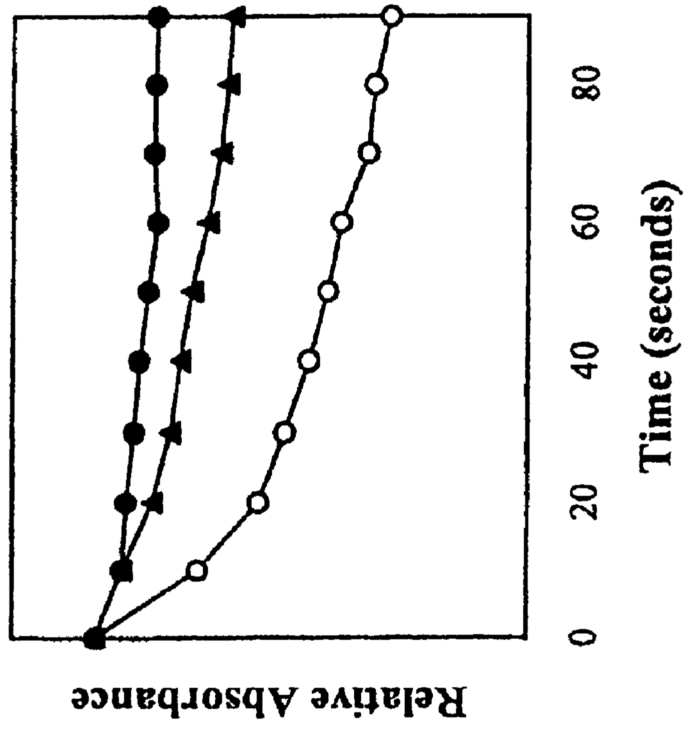
FIGS. 5A–5B are graphs showing lack of amino acid transport through PorB. Liposome swelling analysis of PorB (panel A) and the outer membrane of *E. coli* expressing MOMP (panel B). Liposomes were made as described and 0.017 ml out of a total of 0.3 ml was diluted in 0.6 ml of isotonic sugar solutions of stachyose, arabinose (open circles) and alanine (closed triangles). The y-axis represents a range of $A_{400}$ 0.15.
Figure 5B:
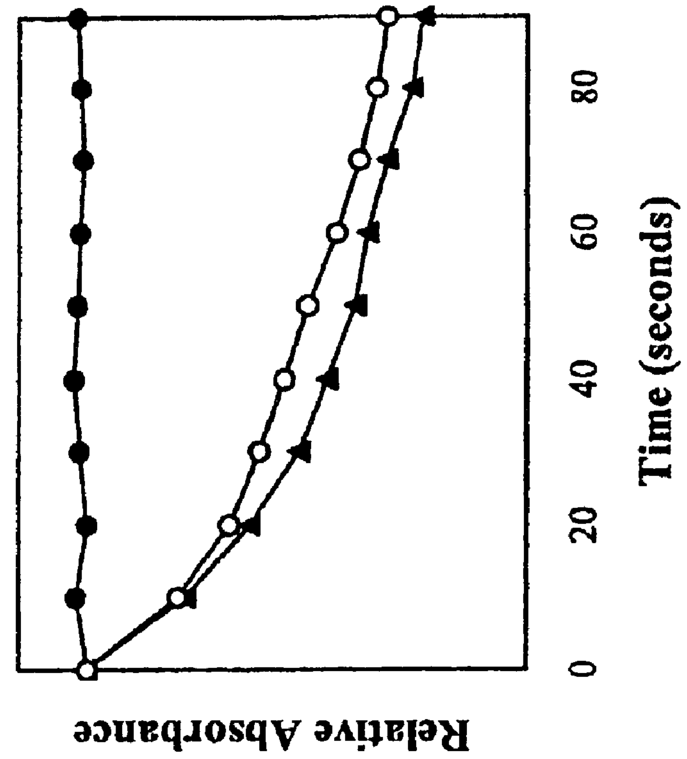

Since *Chlamydia* have been proposed to utilize amino acids from host cells (Ossowski et al (1965) *Isr. J. Med. Sci.* 1:186–193; Hatch et al. (1982) *J. Bacteriol.* 150:379–385; Pearce, (1986) *Ann. Inst. Pasteur Microbiol.* 137A:325–332), diffusion of amino acids through PorB and MOMP were tested using the liposome swelling assay. MOMP liposomes allow for the diffusion of all of the amino acids at different rates based predominantly on size selectivity and alanine and glycine enter through MOMP liposomes slightly faster than arabinose (Jones et al. (2000) *Gene* 258:173–181). In contrast, PorB liposomes did not efficiently allow for any of 20 amino acids to enter liposomes including the small amino acids such as alanine (FIG. 5). These data indicate that PorB is less efficient than MOMP as a non-specific porin.

Example 10

Permeability of Solutes Through PorB

PorB was purified by nickel column chromatography and incorporated into liposomes. Liposomes enriched for MOMP were used to compare the pore-forming activity of PorB. As shown above, PorB porin function, unlike MOMP, is inefficient in the diffusion of amino acids, even amino acids smaller in molecular weight than arabinose, such as glycine and alanine. MOMP porin activity is detected using only 1 μg of protein (total outer membrane protein) while 6–10 μg of purified PorB is needed to observe comparable porin activity. This suggests that PorB is much less efficient as a non-specific porin or that the purification process may have resulted in a less functional protein.

Differences in general pore-forming activity, as well as differences in the amount present in the chlamydial outer membrane, suggest a unique role for each of the porins. The presence of PorB in small amounts is difficult to understand unless PorB has a role as a substrate-specific porin that is efficient in the uptake of particular classes of molecules. RT-PCR analysis and cell staining at various time points indicated that this protein is expressed throughout the developmental cycle. Thus PorB expression is not differentially regulated.

In order to determine if PorB had specificity for any molecule(s), the genome sequence was studied to determine if the inferred biology of *Chlamydia* could provide an idea of which molecules *Chlamydia* might need to obtain from the host. This analysis provided a list of orthologs of transporters that are important in the translocation of solutes across the inner membrane, including amino acid, polysaccharide, oligopeptide, and dicarboxylate transporters (Stephens et al. (1998) *Science* 282:754–759). Previous analysis of MOMP porin activity showed that amino acids, mono- and di-saccharide and oligopeptides enter efficiently through MOMP (Jones et al. (2000) *Gene* 258:173–181). However, PorB did not allow for the efficient entry of either amino acids or polysaccharides. The presence of an ortholog to an inner membrane dicarboxylate transporter, and that *Chlamydia* appears to have a truncated TCA cycle, suggest that chlamydiae may require exogenous α-ketoglutarate from the host cell. Therefore, the hypothesis that dicarboxylates could enter through the chlamydial outer membrane was tested by measuring α-ketoglutarate diffusion through the two known porins, PorB and MOMP.

Figure 6B:
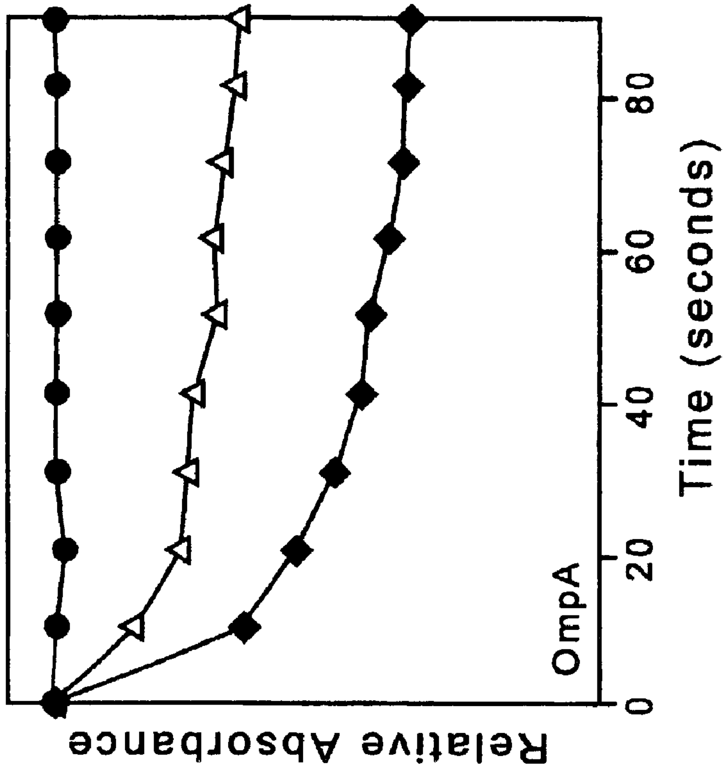
FIGS. 6A and 6B are graphs showing the results of a liposome swelling analysis of PorB (panel A) and the outer membrane of *E. coli* expressing MOMP (OmpA) (panel B). Isotonic solutions of stachyose (closed circles), arabinose (closed diamonds) and α-ketoglutarate (open triangles). The y-axis represents a range of $A_{400}$ 0.15.
Figure 6A:
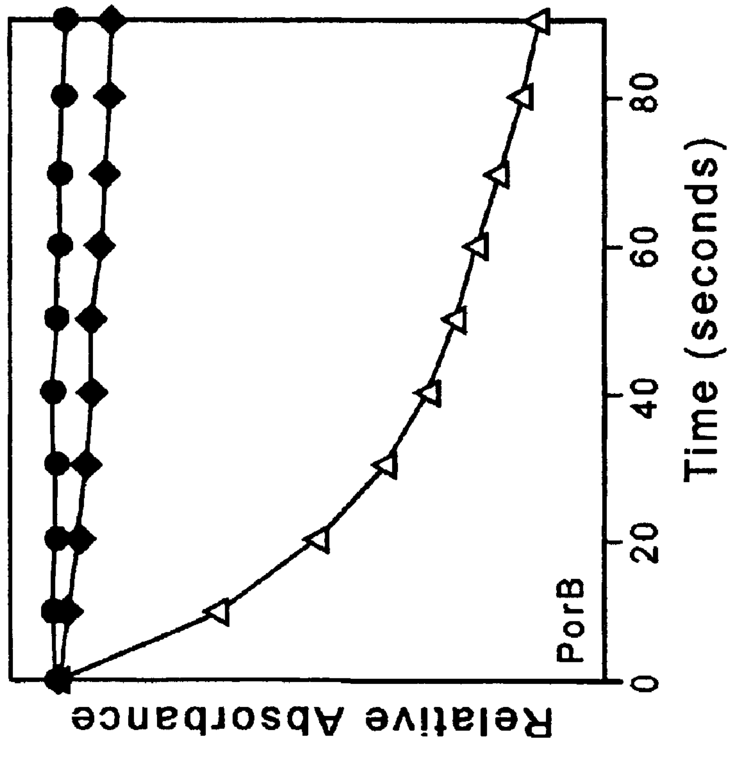

The liposome swelling assay with PorB and MOMP showed that the diffusion of α-ketoglutarate was more efficient through PorB than MOMP (FIG. 6). No diffusion of α-ketoglutarate was seen with liposomes without protein, as well as liposomes with another chlamydial outer membrane protein (Omp85) that was purified by the same method as PorB. Chlamydial Omp85 was used as a control protein that was cloned, expressed in *E. coli* and purified by the same method used to purify PorB. *E. coli* not expressing PorB, which was treated the same way as *E. coli* expressing PorB, was purified by nickel column chromatography and the column eluate was used as a control in all of the assays to verify that no *E. coli* contaminants were responsible for the porin activity observed.

Figure 7:
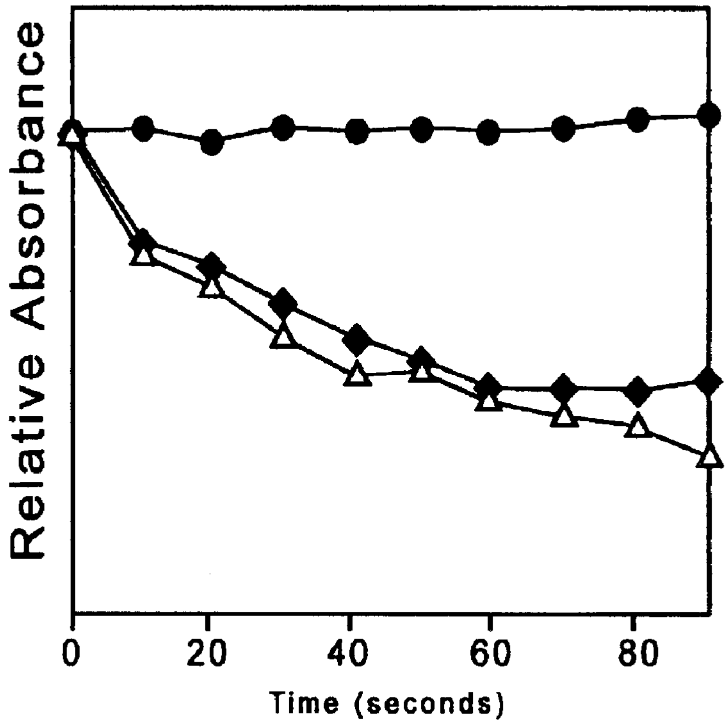
FIG. 7 is a graph showing the results of a liposome swelling assay to control for effects of ions that may be present in the test solute. Liposomes containing $NAD^+$, stachyose, and imidazone-NAD were diluted in isotonic test solutions of citrate (closed circles), oxaloacetate (closed diamonds), and α-ketoglutarate (open triangles). The y-axis represents a range of $A_{400}$ 0.15.

One concern with the liposome assays was the possible influence of ions present in anionic solutes, such as α-ketoglutarate, that may cause ion fluxes potentially confounding the results of the assay. A liposome assay to control for the possibility of ion fluxes (Nikaido and Rosenberg (1983) *J. Bacteriol.* 153:241–252) was used to confirm the swelling assay results. Liposomes were made with $NAD^+$-imidazole and stachyose to counteract any ion fluxes that may result from the presence of contaminating ions in the α-ketoglutarate solute used for the assay. This assay confirmed that the results in the initial liposome assays were not the result of ion fluxes and that oxaloacetate also entered efficiently through PorB while citrate did not enter (FIG. 7).

Figure 8:
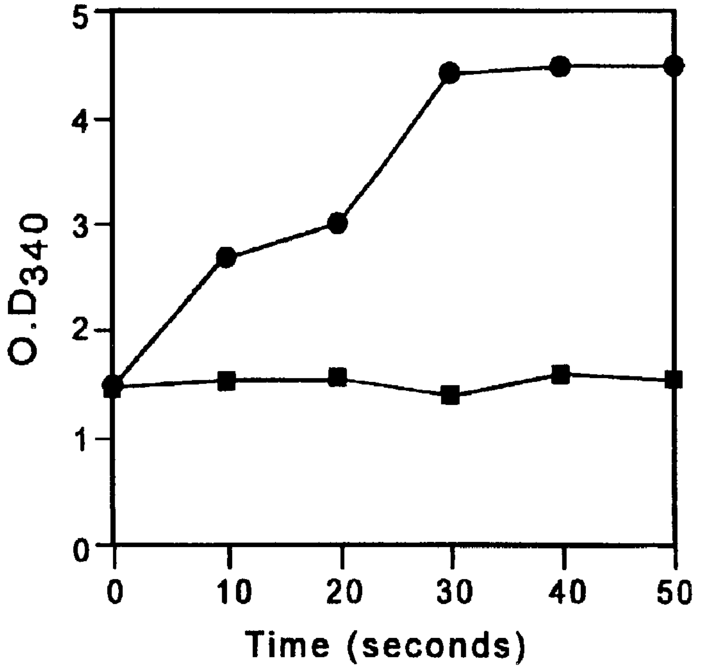
FIG. 8 is a graph showing enzyme-linked liposome assay testing of the entry and oxidation of α-ketoglutarate. The formation of NADH using liposomes containing PorB (closed circles) or lacking PorB (closed squares) was measured by an increase in $O.D._{340}$.

An enzyme-linked liposome assay was used to further show that the α-ketoglutarate was entering through PorB. The liposomes were made with α-ketoglutarate dehydrogenase and $NAD^+$ inside and washed The substrate, α-ketoglutarate, was added to the outside of the liposomes and then the liposomes were measured for the formation of NADH by the increase in the $O.D._{340}$. This shows that α-ketoglutarate entered through PorB unlike the control liposomes which did not allow α-ketoglutarate to enter inside and result in the formation of NADH (FIG. 8).

Example 11

TCA Cycle Molecules Enter Through PorB

Figure 9:
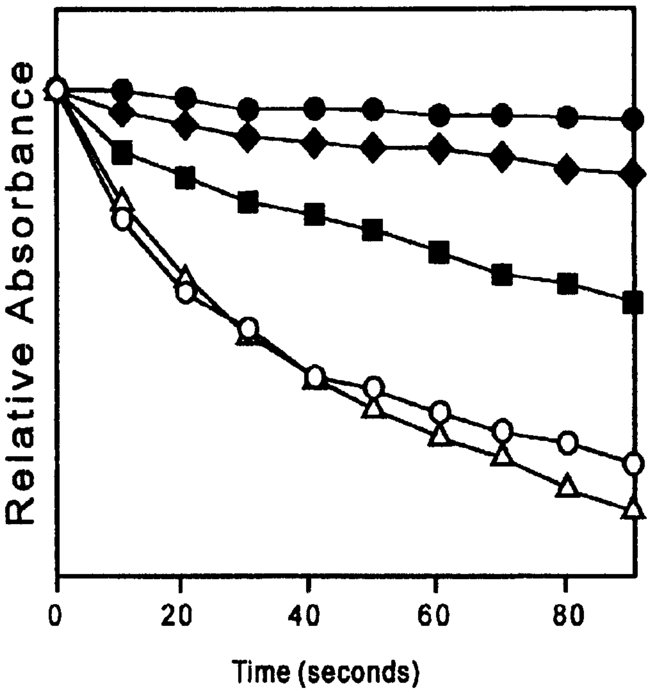
FIG. 9 is a graph showing liposome swelling analysis of PorB using TCA-cycle intermediates. Isotonic sugar solutions of stachyose (closed circles), arabinose (closed diamonds), α-ketoglutarate (open triangles), malate (closed squares) and succinate (open circles). The y-axis represents a range of $A_{400}$ 0.15.

Since α-ketoglutarate efficiently entered through PorB, a number of other TCA cycle intermediates were tested to assess whether this porin was specific for the α-ketoglutarate substrate. Succinate (and oxaloacetate) enter PorB with similar rates to α-ketoglutarate; however, malate did not enter efficiently (FIG. 9). Citrate did not enter through PorB.

Example 12

Permeability Specificity Studies with PorB

Figure 10:
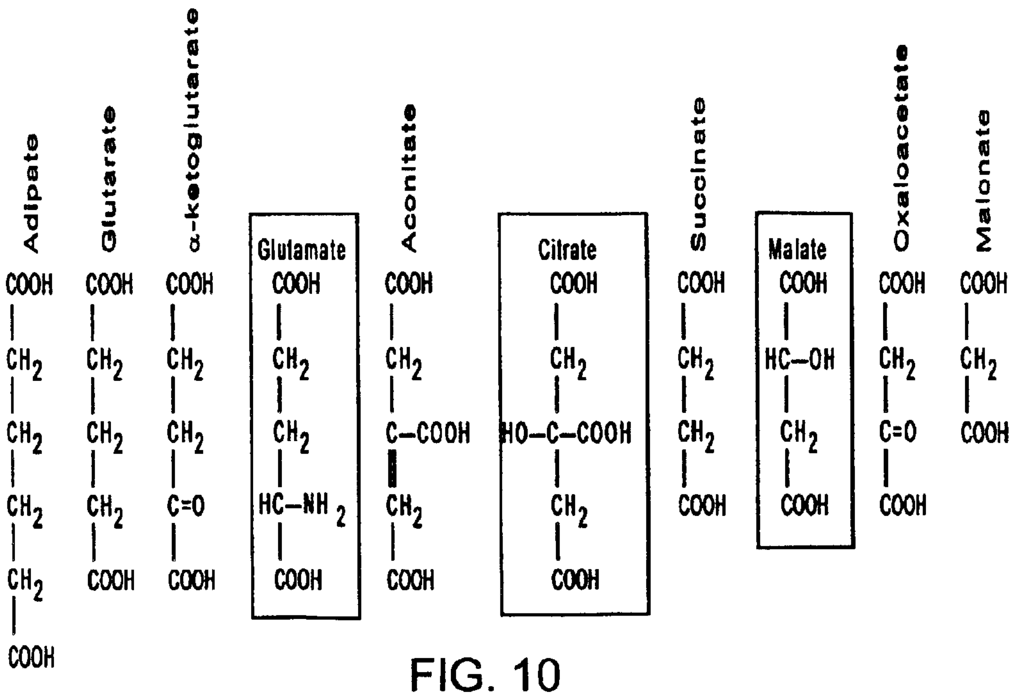
FIG. 10 is a schematic showing the structures of compounds tested for diffusion into liposomes containing PorB. Compounds in shaded boxes were not efficiently transported by PorB.

Since dicarboxylates of the TCA cycle were tested and diffused through PorB, other molecular analogues were studied to determine the capability of PorB to distinguish between related molecules (FIG. 10). A difference in carbon-chain lengths represented by adipate, glutarate, succinate, and malonate did not show marked differences in diffusion compared to α-ketoglutarate, although 6-carbon adipate and 3-carbon malonate entered through PorB at a slightly slower rate. Thus PorB did not discriminate between different substrate chain lengths. The effects of small side groups using analogues that differed only by specific side groups were tested. For example, α-ketoglutarate and glutarate entered through PorB efficiently, but not glutamate that is similar in structure. The presence of the amino group seems to retard the diffusion of glutamate and this likely explains why other amino acids do not enter into PorB efficiently. A comparison of 5-carbon compounds citrate and aconitate with only the addition of a hydroxyl group to citrate prevented the entry of citrate through PorB. Four-carbon malate and succinate also differ by the presence of a hydroxyl group and the diffusion rate was retarded for malate. Therefore, PorB can discern between very similar compounds to allow for specific selectivity, suggesting a substrate-specific selective porin. These findings show that PorB facilitates the diffusion α-ketoglutarate and other select dicarboxylates to enter chlamydial outer membranes efficiently.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for eliciting production of antibodies to a *Chlamydia bacterium* in a mammalian subject, the method comprising:

administering to a mammalian subject a chlamydial PorB polypeptide in an amount sufficient to elicit production of antibodies, which antibodies neutralize infection by *Chlamydial* bacteria of different serovars;

wherein said administering primes an immune response in the subject against infection by *Chlamydia* bacteria of different serovars.

2. The method of claim 1, wherein the chlamydial PorB polypeptide is a PorB polypeptide of *Chlamydia trachomatis*.

3. The method of claim 1, wherein the chlamydial PorB polypeptide is a PorB polypeptide of *Chlamydia pneumoniae*.

4. The method of claim 1, wherein the chlamydial PorB polypeptide is a PorB polypeptide of *Chlamydia psittaci*.

5. The method of claim 1, wherein the chlamydial PorB polypeptide is encoded in a nucleic acid adapted for expression in the subject.

6. The method of claim 1, wherein the chlamydial PorB polypeptide is provided in a recombinant microorganism.

7. The method of claim 6, wherein the recombinant microorganism is a recombinant virus comprising a chlamydial PorB polypeptide-encoding polynucleotide for expression in the subject.

8. The method of claim 1, wherein said administering is subcutaneous, intramuscular, intradermal, or intravenous.

9. The method of claim 1, wherein the chlamydial PorB polypeptide is provided as a nucleic acid encoding the PorB polypeptide adapted for expression in the subject, and wherein said administering is subcutaneous, transdermal, subdermal, intradermal, topical, or intramuscular.

10. The method of claim 1, wherein the neutralizing antibodies effect neutralization of at least two species of *Chlamydia*.

* * * * *

SEQUENCE LISTING

```
<160> NUMBER OF SEQ ID NOS: 6

<210> SEQ ID NO 1
<211> LENGTH: 1023
<212> TYPE: DNA
<213> ORGANISM: C. trachomatis
<220> FEATURE:
<221> NAME/KEY: CDS
<222> LOCATION: (1)...(1020)

<400> SEQUENCE: 1

atg agt agc aag cta gtg aac tat ctc cgt ttg act ttc cta tct ttt       48
Met Ser Ser Lys Leu Val Asn Tyr Leu Arg Leu Thr Phe Leu Ser Phe
 1               5                  10                  15

tta ggg atc gca tct act tca tta gac gct atg cct gcg ggg aat ccg       96
Leu Gly Ile Ala Ser Thr Ser Leu Asp Ala Met Pro Ala Gly Asn Pro
            20                  25                  30

gcg ttt cca gtc atc ccg ggg att aat att gaa cag aaa aat gcc tgt      144
Ala Phe Pro Val Ile Pro Gly Ile Asn Ile Glu Gln Lys Asn Ala Cys
        35                  40                  45

tct ttc gat tta tgt aat tct tat gat gta cta tcc gca ctg tcc ggt      192
```

-continued

```
Ser Phe Asp Leu Cys Asn Ser Tyr Asp Val Leu Ser Ala Leu Ser Gly
     50                  55                  60

aac ctg aag ctc tgc ttc tgc gga gat tat atc ttt tca gaa gaa gct      240
Asn Leu Lys Leu Cys Phe Cys Gly Asp Tyr Ile Phe Ser Glu Glu Ala
 65                  70                  75                  80

cag gta aaa gat gtc cct gtc gtt acc tct gtg aca aca gct ggg gtt      288
Gln Val Lys Asp Val Pro Val Val Thr Ser Val Thr Thr Ala Gly Val
                 85                  90                  95

ggt cct tct cct gat att act tcg aca acc aaa acg cga aat ttc gat      336
Gly Pro Ser Pro Asp Ile Thr Ser Thr Thr Lys Thr Arg Asn Phe Asp
            100                 105                 110

ctc gtg aac tgt aat ctc aat aca aac tgt gta gct gta gct ttt tcc      384
Leu Val Asn Cys Asn Leu Asn Thr Asn Cys Val Ala Val Ala Phe Ser
        115                 120                 125

ctt cct gat cgt tcg ctg agc gcg att cct ctg ttt gat gtg agt ttc      432
Leu Pro Asp Arg Ser Leu Ser Ala Ile Pro Leu Phe Asp Val Ser Phe
    130                 135                 140

gaa gtg aaa gta gga gga ctg aaa caa tac tac cgc ctt ccc atg aat      480
Glu Val Lys Val Gly Gly Leu Lys Gln Tyr Tyr Arg Leu Pro Met Asn
145                 150                 155                 160

gcc tat cga gac ttc acc tcg gaa cct ctc aat tct gaa tca gaa gtt      528
Ala Tyr Arg Asp Phe Thr Ser Glu Pro Leu Asn Ser Glu Ser Glu Val
                165                 170                 175

acg gac ggg atg att gaa gta cag tcc aat tac gga ttt gtt tgg gat      576
Thr Asp Gly Met Ile Glu Val Gln Ser Asn Tyr Gly Phe Val Trp Asp
            180                 185                 190

gtt agc ttg aaa aaa gtc ata tgg aaa gat ggc gtt tcc ttt gta ggc      624
Val Ser Leu Lys Lys Val Ile Trp Lys Asp Gly Val Ser Phe Val Gly
        195                 200                 205

gtc ggt gca gac tat cgc cat gct tct tgc cct att gac tac atc att      672
Val Gly Ala Asp Tyr Arg His Ala Ser Cys Pro Ile Asp Tyr Ile Ile
    210                 215                 220

gca aac agt caa gct aat cca gaa gta ttc atc gct gac tcg gat ggg      720
Ala Asn Ser Gln Ala Asn Pro Glu Val Phe Ile Ala Asp Ser Asp Gly
225                 230                 235                 240

aaa ctg aac ttc aag gag tgg agt gtc tgc gta ggt ctt act acc tat      768
Lys Leu Asn Phe Lys Glu Trp Ser Val Cys Val Gly Leu Thr Thr Tyr
                245                 250                 255

gtg aat gac tac gtt ctt cct tac tta gcg ttt tct ata ggg agt gtt      816
Val Asn Asp Tyr Val Leu Pro Tyr Leu Ala Phe Ser Ile Gly Ser Val
            260                 265                 270

tct cgc caa gct ccg gac gac agc ttc aaa aaa tta gaa gat cgc ttc      864
Ser Arg Gln Ala Pro Asp Asp Ser Phe Lys Lys Leu Glu Asp Arg Phe
        275                 280                 285

act aac ctc aaa ttt aaa gtt cgt aaa att acc agc tct cat cgt gga      912
Thr Asn Leu Lys Phe Lys Val Arg Lys Ile Thr Ser Ser His Arg Gly
    290                 295                 300

aac atc tgc atc gga gcg aca aac tat gtc gcc gat aac ttc ttc tac      960
Asn Ile Cys Ile Gly Ala Thr Asn Tyr Val Ala Asp Asn Phe Phe Tyr
305                 310                 315                 320

aac gta gaa gga aga tgg gga agc cag cgc gct gtg aac gtc tcc gga     1008
Asn Val Glu Gly Arg Trp Gly Ser Gln Arg Ala Val Asn Val Ser Gly
                325                 330                 335

gga ttc caa ttc taa                                                 1023
Gly Phe Gln Phe
            340
```

<210> SEQ ID NO 2
<211> LENGTH: 340
<212> TYPE: PRT

-continued

<213> ORGANISM: C. trachomatis

<400> SEQUENCE: 2

```
Met Ser Ser Lys Leu Val Asn Tyr Leu Arg Leu Thr Phe Leu Ser Phe
 1               5                  10                  15

Leu Gly Ile Ala Ser Thr Ser Leu Asp Ala Met Pro Ala Gly Asn Pro
            20                  25                  30

Ala Phe Pro Val Ile Pro Gly Ile Asn Ile Glu Gln Lys Asn Ala Cys
        35                  40                  45

Ser Phe Asp Leu Cys Asn Ser Tyr Asp Val Leu Ser Ala Leu Ser Gly
    50                  55                  60

Asn Leu Lys Leu Cys Phe Cys Gly Asp Tyr Ile Phe Ser Glu Glu Ala
65                  70                  75                  80

Gln Val Lys Asp Val Pro Val Val Thr Ser Val Thr Thr Ala Gly Val
                85                  90                  95

Gly Pro Ser Pro Asp Ile Thr Ser Thr Thr Lys Thr Arg Asn Phe Asp
            100                 105                 110

Leu Val Asn Cys Asn Leu Asn Thr Asn Cys Val Ala Val Ala Phe Ser
        115                 120                 125

Leu Pro Asp Arg Ser Leu Ser Ala Ile Pro Leu Phe Asp Val Ser Phe
    130                 135                 140

Glu Val Lys Val Gly Gly Leu Lys Gln Tyr Tyr Arg Leu Pro Met Asn
145                 150                 155                 160

Ala Tyr Arg Asp Phe Thr Ser Glu Pro Leu Asn Ser Glu Ser Glu Val
                165                 170                 175

Thr Asp Gly Met Ile Glu Val Gln Ser Asn Tyr Gly Phe Val Trp Asp
            180                 185                 190

Val Ser Leu Lys Lys Val Ile Trp Lys Asp Gly Val Ser Phe Val Gly
        195                 200                 205

Val Gly Ala Asp Tyr Arg His Ala Ser Cys Pro Ile Asp Tyr Ile Ile
    210                 215                 220

Ala Asn Ser Gln Ala Asn Pro Glu Val Phe Ile Ala Asp Ser Asp Gly
225                 230                 235                 240

Lys Leu Asn Phe Lys Glu Trp Ser Val Cys Val Gly Leu Thr Thr Tyr
                245                 250                 255

Val Asn Asp Tyr Val Leu Pro Tyr Leu Ala Phe Ser Ile Gly Ser Val
            260                 265                 270

Ser Arg Gln Ala Pro Asp Asp Ser Phe Lys Lys Leu Glu Asp Arg Phe
        275                 280                 285

Thr Asn Leu Lys Phe Lys Val Arg Lys Ile Thr Ser Ser His Arg Gly
    290                 295                 300

Asn Ile Cys Ile Gly Ala Thr Asn Tyr Val Ala Asp Asn Phe Phe Tyr
305                 310                 315                 320

Asn Val Glu Gly Arg Trp Gly Ser Gln Arg Ala Val Asn Val Ser Gly
                325                 330                 335

Gly Phe Gln Phe
            340
```

<210> SEQ ID NO 3
<211> LENGTH: 393
<212> TYPE: PRT
<213> ORGANISM: C. trachomatis

<400> SEQUENCE: 3

```
Met Lys Lys Leu Leu Lys Ser Val Leu Val Phe Ala Ala Leu Ser Ser
```

-continued

```
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Ala Thr Trp Cys Asp Ala Ile Ser Met Arg Val Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Lys Pro Thr Thr Asp Thr Gly Asn Ser Ala
                85                  90                  95

Ala Pro Ser Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Thr Ser Gly
    130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
                165                 170                 175

Ser Phe Asp Gln Ser Val Val Glu Leu Tyr Thr Asp Thr Thr Phe Ala
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
    290                 295                 300

Ala Gln Pro Lys Ser Ala Thr Ala Ile Phe Asp Thr Thr Thr Leu Asn
305                 310                 315                 320

Pro Thr Ile Ala Gly Ala Gly Asp Val Lys Thr Gly Ala Glu Gly Gln
                325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
        355                 360                 365

Asp Lys Tyr Ala Val Thr Val Glu Thr Arg Leu Ile Asp Glu Arg Ala
    370                 375                 380

Ala His Val Asn Ala Gln Phe Arg Phe
385                 390
```

<210> SEQ ID NO 4
<211> LENGTH: 345
<212> TYPE: PRT
<213> ORGANISM: C. pneumonia -continued

<400> SEQUENCE: 4

```
Met Asn Ser Lys Met Leu Lys His Leu Arg Leu Ala Thr Leu Ser Phe
 1              5                   10                  15

Ser Met Phe Phe Gly Ile Val Ser Ser Pro Ala Val Tyr Ala Leu Gly
            20                  25                  30

Ala Gly Asn Pro Ala Ala Pro Val Leu Pro Gly Val Asn Pro Glu Gln
        35                  40                  45

Thr Gly Trp Cys Ala Phe Gln Leu Cys Asn Ser Tyr Asp Leu Phe Ala
    50                  55                  60

Ala Leu Ala Gly Ser Leu Lys Phe Gly Phe Tyr Gly Asp Tyr Val Phe
65                  70                  75                  80

Ser Glu Ser Ala His Ile Thr Asn Val Pro Val Ile Thr Ser Val Thr
                85                  90                  95

Thr Ser Gly Thr Gly Thr Thr Pro Thr Ile Thr Ser Thr Thr Lys Asn
            100                 105                 110

Val Asp Phe Asp Leu Asn Asn Ser Ser Ile Ser Ser Ser Cys Val Phe
        115                 120                 125

Ala Thr Ile Ala Leu Gln Glu Thr Ser Pro Ala Ala Ile Pro Leu Leu
    130                 135                 140

Asp Ile Ala Phe Thr Ala Arg Val Gly Gly Leu Lys Gln Tyr Tyr Arg
145                 150                 155                 160

Leu Leu Pro Leu Asn Ala Tyr Arg Asp Phe Thr Ser Asn Pro Leu Asn
                165                 170                 175

Ala Glu Ser Glu Val Thr Asp Gly Leu Ile Glu Val Gln Ser Asp Tyr
            180                 185                 190

Gly Ile Val Trp Gly Leu Ser Leu Gln Lys Val Leu Trp Lys Asp Gly
        195                 200                 205

Val Ser Phe Val Gly Val Ser Ala Asp Tyr Arg His Gly Ser Ser Pro
    210                 215                 220

Ile Asn Tyr Ile Ile Val Tyr Val Lys Ala Asn Pro Glu Ile Tyr Phe
225                 230                 235                 240

Asp Ala Thr Asp Gly Asn Leu Ser Tyr Lys Glu Trp Ser Ala Ser Ile
                245                 250                 255

Gly Ile Ser Thr Tyr Leu Asn Asp Tyr Val Leu Pro Tyr Ala Ser Val
            260                 265                 270

Ser Ile Gly Asn Thr Ser Arg Lys Ala Pro Ser Asp Ser Phe Thr Glu
        275                 280                 285

Leu Glu Lys Trp Phe Thr Asn Phe Lys Phe Lys Ile Arg Lys Ile Thr
    290                 295                 300

Asn Phe Asp Arg Val Asn Phe Cys Phe Gly Thr Thr Cys Cys Ile Ser
305                 310                 315                 320

Asn Asn Phe Tyr Tyr Ser Val Glu Gly Arg Trp Gly Tyr Gln Arg Ala
                325                 330                 335

Ile Asn Ile Thr Ser Gly Leu Gln Phe
            340                 345
```

<210> SEQ ID NO 5
<211> LENGTH: 340
<212> TYPE: PRT
<213> ORGANISM: C. trachomatis (L2)

<400> SEQUENCE: 5

```
Met Ser Ser Lys Leu Val Asn Tyr Leu Arg Leu Thr Phe Leu Ser Phe
 1              5                   10                  15
```

-continued

```
Leu Gly Ile Ala Ser Thr Ser Leu Asp Ala Met Pro Ala Gly Asn Pro
            20                  25                  30

Ala Phe Pro Val Ile Pro Gly Ile Asn Ile Glu Gln Lys Asn Ala Cys
        35                  40                  45

Ser Phe Asp Leu Cys Asn Ser Tyr Asp Val Leu Ser Ala Leu Ser Gly
    50                  55                  60

Asn Leu Lys Leu Cys Phe Phe Gly Asp Tyr Ile Phe Ser Glu Glu Ala
65                  70                  75                  80

Gln Val Lys Asp Val Pro Val Val Thr Ser Val Thr Thr Cys Gly Ile
                85                  90                  95

Gly Pro Ser Pro Asn Ile Thr Ser Thr Thr Lys Thr Arg Asn Phe Asp
            100                 105                 110

Leu Val Asn Cys Asn Leu Asn Glx Asn Cys Ala Ala Val Ala Phe Ser
        115                 120                 125

Leu Pro Asp Arg Ser Leu Ser Ala Ile Pro Leu Phe Asp Val Ser Phe
    130                 135                 140

Glu Val Lys Val Gly Gly Leu Lys Gln Tyr Tyr Arg Leu Pro Met Asn
145                 150                 155                 160

Ala Tyr Arg Asp Phe Thr Ser Glu Pro Leu Asn Ser Glu Ser Glu Val
                165                 170                 175

Thr Asp Gly Met Ile Glu Val Gln Ser Asn Tyr Gly Phe Val Trp Asp
            180                 185                 190

Val Ser Leu Lys Lys Val Ile Trp Lys Asp Gly Val Ser Phe Val Gly
        195                 200                 205

Val Gly Ala Asp Tyr Arg His Ala Ser Cys Pro Ile Asp Tyr Ile Ile
    210                 215                 220

Ala Asn Ser Gln Ala Asn Pro Glu Val Phe Ile Ala Asp Ser Asp Gly
225                 230                 235                 240

Lys Leu Asn Phe Lys Glu Trp Ser Val Cys Val Gly Leu Thr Thr Tyr
                245                 250                 255

Val Asn Asp Tyr Val Leu Pro Tyr Leu Ala Phe Ser Ile Gly Ser Val
            260                 265                 270

Ser Arg Gln Ala Pro Asp Asp Ser Phe Lys Lys Leu Glu Asp Arg Phe
        275                 280                 285

Thr Asn Leu Lys Phe Lys Val Arg Lys Ile Thr Ser Ser His Arg Gly
    290                 295                 300

Asn Ile Cys Ile Gly Ala Thr Asn Tyr Ile Ala Asp Asn Phe Phe Tyr
305                 310                 315                 320

Asn Val Glu Gly Arg Trp Gly Ser Gln Arg Ala Val Asn Val Ser Gly
                325                 330                 335

Gly Phe Gln Phe
            340


<210> SEQ ID NO 6
<211> LENGTH: 340
<212> TYPE: PRT
<213> ORGANISM: C. trachomatis (C)

<400> SEQUENCE: 6

Met Ser Ser Lys Leu Val Asn Tyr Leu Arg Leu Thr Phe Leu Ser Phe
 1               5                  10                  15

Leu Gly Ile Ala Ser Thr Ser Leu Asp Ala Met Pro Ala Gly Asn Pro
            20                  25                  30

Ala Phe Pro Val Ile Pro Gly Ile Asn Ile Glu Gln Lys Asn Ala Cys
```

-continued

```
        35                  40                  45

Ser Phe Asp Leu Cys Asn Ser Tyr Asp Val Leu Ser Ala Leu Ser Gly
    50                  55                  60

Asn Leu Lys Leu Cys Phe Cys Gly Asp Tyr Ile Phe Ser Glu Glu Ala
65                  70                  75                  80

Gln Val Lys Asp Val Pro Val Val Thr Ser Met Thr Thr Ala Gly Val
                85                  90                  95

Gly Pro Ser Pro Asp Ile Thr Ser Thr Thr Lys Thr Arg Asn Phe Asp
            100                 105                 110

Leu Val Asn Cys Asn Leu Asn Thr Asn Cys Val Ala Val Ala Phe Ser
        115                 120                 125

Leu Pro Asp Arg Ser Leu Ser Ala Ile Pro Leu Phe Asp Val Ser Phe
    130                 135                 140

Glu Val Lys Val Gly Gly Leu Lys Gln Tyr Tyr Arg Leu Pro Met Asn
145                 150                 155                 160

Ala Tyr Arg Asp Phe Thr Ser Glu Pro Leu Asn Ser Glu Ser Glu Val
                165                 170                 175

Thr Asp Gly Met Ile Glu Val Gln Ser Asn Tyr Gly Phe Val Trp Asp
            180                 185                 190

Val Ser Leu Lys Lys Val Ile Trp Lys Asp Gly Val Ser Phe Val Gly
        195                 200                 205

Val Gly Ala Asp Tyr Arg His Ala Ser Cys Pro Ile Asp Tyr Ile Ile
    210                 215                 220

Ala Asn Ser Gln Ala Asn Pro Glu Val Phe Ile Ala Asp Ser Asp Gly
225                 230                 235                 240

Lys Leu Asn Phe Lys Glu Trp Ser Val Cys Val Gly Leu Thr Thr Tyr
                245                 250                 255

Val Asn Asp Tyr Val Leu Pro Tyr Leu Ala Phe Ser Ile Gly Ser Val
            260                 265                 270

Ser Arg Gln Ala Pro Asp Asp Ser Phe Lys Lys Leu Glu Asp Arg Phe
        275                 280                 285

Thr Asn Leu Lys Phe Lys Val Arg Lys Ile Thr Ser Ser His Arg Gly
    290                 295                 300

Asn Ile Cys Ile Gly Ala Thr Asn Tyr Ile Ala Asp Asn Phe Phe Tyr
305                 310                 315                 320

Asn Val Glu Gly Arg Trp Gly Ser Gln Arg Ala Val Asn Val Ser Gly
                325                 330                 335

Gly Phe Gln Phe
            340
```